(12) United States Patent
Holvoet et al.

US007229776B2

(10) Patent No.: US 7,229,776 B2
(45) Date of Patent: Jun. 12, 2007

(54) ASSAYS, ANTIBODIES, AND STANDARDS FOR DETECTION OF OXIDIZED AND MDA-MODIFIED LOW DENSITY LIPOPROTEINS

(75) Inventors: Paul Noel Holvoet, Kessel-Lo (BE); Désiré José Collen, London (GB)

(73) Assignee: Leuven Research & Development VZW (BE)

( * ) Notice: Subject to any disclaimer, the term of this patent is extended or adjusted under 35 U.S.C. 154(b) by 559 days.

(21) Appl. No.: 10/802,709

(22) Filed: Mar. 17, 2004

(65) Prior Publication Data

US 2005/0084917 A1 Apr. 21, 2005

Related U.S. Application Data

(62) Division of application No. 09/446,259, filed as application No. PCT/EP97/03493 on Jul. 1, 1997, now Pat. No. 6,727,102.

(30) Foreign Application Priority Data

Jun. 20, 1997 (EP) ...................... PCT/EP97/03287

(51) Int. Cl.
G01N 33/53 (2006.01)
A61K 39/395 (2006.01)
(52) U.S. Cl. ..................... 435/7.1; 435/70.21; 435/325; 436/512; 436/547; 424/130.1; 424/178.1; 530/387.1
(58) Field of Classification Search ................. 435/7.1, 435/70.21, 325; 436/512, 547; 424/130.1, 424/178.1; 530/387.1
See application file for complete search history.

(56) References Cited

U.S. PATENT DOCUMENTS

| 5,024,829 | A | 6/1991 | Berger et al. |
|---|---|---|---|
| 5,026,537 | A | 6/1991 | Daddona et al. |
| 5,046,499 | A | 9/1991 | Berger |
| 5,120,834 | A | 6/1992 | Gargan et al. |
| 5,196,324 | A | 3/1993 | Bumol et al. |
| 5,223,410 | A | 6/1993 | Gargan et al. |
| 5,362,649 | A | 11/1994 | Schwertner |
| 5,380,667 | A | 1/1995 | Schwertner |
| 5,396,886 | A | 3/1995 | Cuypers |
| 5,453,359 | A | 9/1995 | Gargan et al. |
| 5,487,892 | A | 1/1996 | Gargan |
| 5,597,726 | A | 1/1997 | Bumol et al. |
| 5,604,105 | A | 2/1997 | Jackowski |
| 5,658,729 | A | 8/1997 | Hayden et al. |
| 5,690,103 | A | 11/1997 | Groth et al. |
| 5,710,008 | A | 1/1998 | Jackowski |
| 5,731,208 | A | 3/1998 | Henicke |
| 5,756,067 | A | 5/1998 | Redgrave et al. |
| 6,040,147 | A | 3/2000 | Ridker et al. |
| 6,309,888 | B1 | 10/2001 | Holvoet |
| 6,727,102 | B1 | 4/2004 | Holvoet et al. |
| 2003/0100486 | A1 | 5/2003 | Ridker |
| 2003/0152566 | A1 | 8/2003 | Schonbeck et al. |

FOREIGN PATENT DOCUMENTS

| EP | 0 327 418 A1 | 8/1989 |
|---|---|---|
| EP | 0 484 863 A1 | 5/1992 |
| EP | 0 433 088 B1 | 6/1997 |
| JP | 4-173096 | 6/1992 |
| JP | KOKAI 8-304395 | 11/1996 |
| JP | KOKAI 9-5323 | 10/1997 |
| WO | WO 94/23302 | 10/1994 |
| WO | WO 98/59248 | 12/1998 |
| WO | WO 00/14548 | 3/2000 |

OTHER PUBLICATIONS

Adams JE, 3d, Bodor GS, Davila-Roman VG, Delmez JA, Apple FS, Ladenson JH, Jaffe AS. "Cardiac Troponin I. A Marker With High Specificity For Cardiac Injury," *Circulation* 1993; 88(1): 101-106.

American Biogenetic Sciences Inc. *1995 Annual Report*. 24 pages (1995).

American Biogenetic Sciences. *Focus on Diagnostic Tests: A Technology Analysis*. Updated Full Report. 33 pages. Paisley and Habermas, Inc. (Jun. 3, 1996).

American Biogenetic Sciences, Inc., "Renal dialysis joint venture announced by American Biogenetic Sciences, Inc. and Gull Laboratories, Inc." News Release (Sep. 26, 1996).

American Biogenetic Sciences, Inc. Jesup & Lamont Securities Corporation, "New Buy Recommendation dated Mar. 28, 1996" (12 pages).

Antman EM, Tanasijevic MJ, Thompson B, Schactman M, McCabe CH, Cannon CP, Fischer GA, Fung AY, Thompson C, Wybenga D, Braunwald E. "Cardiac-Specific Troponin I Levels To Predict The Risk Of Mortality In Patients With Acute Coronary Syndromes," *N. Eng. J. Med.* 1996; 335(18): 1342-1349.

AtheroGenics, Inc. Printout of Web Site (WWW.ATHEROGENICS.COM). Home page and "Technology Platform" and "In The News" sections. 17 pages (printed Jun. 8, 1998).

Aviram M, Maor I. "Phospholipase D-Modified Low Density Lipoprotein Is Taken Up By Macrophages At Increased Rate. A Possible Role For Phosphatidic Acid." *J. Clin. Invest.* 1993; 91: 1942-1952.

Berliner JA, Heinecke JW. "The Role Of Oxidized Lipoproteins In Atherogenesis," *Free Radical Biology & Medicine* 1996; 20(5): 707-727.

Boyd H, Gown AM, Wolfbauer G, Chait A. "Direct Evidence For A Protein Recognized By A Monoclonal Antibody Against Oxidatively Modified LDL In Atherosclerotic Lesions From A Watanabe Hyperlipidemic Rabbit," *Am. J. Pathol.* Nov. 1989; 135(5): 815-825.

(Continued)

*Primary Examiner*—Long V. Le
*Assistant Examiner*—Lisa V Cook
(74) *Attorney, Agent, or Firm*—Bryan Cave LLP; Stephen P. Gilbert

(57) ABSTRACT

Immunoassays for malondialdehyde-modified low density lipoprotein (MDA-modified LDL) and oxidized low density lipoprotein (OxLDL), monoclonal antibodies (and the cell lines for them) for use in the assays, and a storage-stable standard (which may be used as a calibrator and/or control) are disclosed. MDA-modified LDL and OxLDL are implicated in atherosclerosis and its etiology.

2 Claims, 6 Drawing Sheets

OTHER PUBLICATIONS

Brody, JE. "Hunt For Heart Disease Tracks A New Suspect." *The New York Times*. 3 pages (Jan. 6, 2004).

Brown MS, Goldstein JL. "Lipoprotein Metabolism In The Macrophage: Implications For Cholesterol Deposition In Atherosclerosis." *Annu. Review Biochem.* 1983; 52: 223-261.

Cartier R, Dagenais F, Hollmann C, Cambron H, Buluran J. "Chronic Exposure To Cyclosporin Affects Endothelial And Smooth Muscle Reactivity In The Rat Aorta." *Ann. Thorac. Surg.* 1994; 58: 789-794.

Chapelle JP. "How Should We proceed When A Myocardial Infarction Is Suspected," *Acta Clinica Belgica* 1984; 39(6): 393-395.

Chen CH, Nguyen HH, Weilbaecher D, Luo S, Gotto Jr. AM, Henry PD. "Basic Fibroblast Growth Factor Reverses Atherosclerotic Impairment Of Human Coronary Angiogenesis-Like Responses In Vitro." *Atherosclerosis* 1995; 116: 261-268.

Chin JH, Azhar S, Hoffman BB. "Inactivation Of Endothelial Derived Relaxing Factor By Oxidized Lipoproteins." *J. Clin. Invest.* 1992; 89: 10-18.

Cockcroft DW, Gault MH. "Prediction of creatinine clearance from serum creatinine." *Nephron* 1976; 16: 31-41.

Crisp SJ, Dunn JM, Rose ML, Barbir M, Yacoub MH. "Antiendothelial Antibodies After Heart Transplantation: The Accelerating Factor In Transplant-Associated Coronary Artery Disease?" *J. Heart Lung Transplant.* 1994; 13(1, Part 1): 81-92.

Declerck PJ, Mombaerts P, Holvoet P, De Mol M, Collen D. "Fibrinolytic Response And Fibrin Fragment D-Dimer Levels In Patients With Deep Vein Thrombosis." *Thromb. Haemost.* 1987; 58(4): 1024-1029.

Degoulet P, Legrain M, Reach I, Aime F, Devries C, Rojas P, Jacobs C. "Mortality Risk Factors In Patients Treated By Chronic Hemodialysis." *Nephron* 1982; 31: 103-110.

Esterbauer H, Jurgens G, Quehenberger O, Koller E. "Autooxidation Of Human Low Density Lipoprotein: Loss Of Polyunsaturated Fatty Acids And Vitamin E And Generation Of Aldehydes." *J. Lipid Res.* 1987; 28: 495-509.

Farber HW, Barnett HF. "Differences In Prostaglandin Metabolism In Cultured Aortic And Pulmonary Arterial Endothelial Cells Exposed To Acute And Chronic Hypoxia." *Circ. Res.* 1991; 68(5): 1446-1457.

Fogelman MA, Schechter I, Seager J, Hokom M, Child JS, Edwards PA. "Malondialdehyde Alteration Of Low Density Lipoproteins Leads To Cholesteryl Ester Accumulation In Human Monocyte-Macrophages." *Proc. Natl. Acad. Sci. USA* 1980; 77(4) : 2214-2218.

Folcik VA, Nivar-Aristy RA, Krajewski LP, Cathcart MK. "Lipoxygenase Contributes To The Oxidation Of Lipids In Human Atherosclerotic Plaques." *J. Clin. Invest.* 1995; 96: 504-510.

Friedman JA, Dwyer JT. "Hyperhomocysteinemia As A Risk Factor For Cardiovascular Disease In Patients Undergoing Hemodialysis." *Nutr. Rev.* 1995; 53(7): 197-201.

Galle J, Bengen J, Schollmeyer P, Wanner C. "Oxidized Lipoprotein (A) Inhibits Endothelium-Dependent Dilation: Prevention By High Density Lipoprotein." *Eur. J. Pharmacol.* 1994; 265: 111-115.

Galle J, Schollmeyer P, Wanner C. "Cyclosporin And Oxidized Low Density Lipoproteins Synergistically Potentiate Vasoconstriction: Influence Of The Endothelium." *Eur. Heart J.* 1993; 14(Suppl. I): 111-117.

Gerrity RG. "The Role Of The Monocyte In Atherogenesis. I. Transition Of Blood-Borne Monocytes Into Foam Cells In Fatty Lesions." *Am. J. Pathol.* 1981; 103(2): 181-190.

Grattan MT, Moreno-Cabral CE, Starnes VA, Oyer PE, Stinson EB, Shumway NE. "Cytomegalovirus Infection Is Associated With Cardiac Allograft Rejection And Atherosclerosis." *J. Am. Med. Assoc.* 1989; 261 (24) : 3561-3566.

Haberland ME, Fogelman AM, Edwards PA. "Specificity Of Receptor-Mediated Recognition Of Malondialdehyde-Modified Low Density Lipoproteins." *Proc. Natl. Acad. Sci USA.* 1982; 79: 1712-1716.

Haberland ME, Olch CL, Fogelman AM. "Role Of Lysines In Mediating Interaction Of Modified Low Density Lipoproteins With The Scavenger Receptor Of Human Monocyte Macrophages." *J. Biol. Chem.* 1984; 259(18): 11305-11311.

Hamm WC, Goldmann BU, Heeschen C, Kreymann G, Berger J, Meinertz T. "Emergency Room Triage Of Patients With Acute Chest Pain By Means Of Rapid Testing For Cardiac Troponin T Or Troponin I." *N. Eng. J. Med.* 1997; 337(23): 1648-1653.

Hamm WC, Goldmann BU, Heeschen C, Kreymann G, Berger J, Meinertz T. "Emergency Room Triage Of Patients With Acute Chest Pain By Means Of Rapid Testing For Cardiac Troponin T Or Troponin I." *N. Eng. J. Med.* 1997; 337(23): 1648-1653. Letters concerning same and authors' reply, published in *N. Eng. J. Med.* 1998; 338(18): 1314-1315.

Hammer A, Kager G, Dohr G, Rabl H, Ghassempur I, Jurgens G. "Generation, Characterization, And Histochemical Application Of Monoclonal Antibodies Selectively Recognizing Osidatively Modified ApoB-Containing Serum Lipoproteins." *Arterioscler. Thromb. Vasc. Biol.* 1995; 15(5): 704-713.

Hansson GK, Libby P. (eds.). *Immune Functions of the Vessel Wall*, vol. II (Harwood Academic Publishers 1996). Chapter 9: Witztum JL, Palinski W. "Autoimmunity To Oxidized Lipoproteins." pp. 159-171.

Havel RJ, Eder HA, Bragdon JH. "The Distribution And Chemical Composition Of Ultracentrifugally Separated Lipoproteins In Human Serum." *J. Clin. Invest.* 1955, 34: 1345-1353.

Heery JM, Kozak M, Stafforini DM, Jones DA, Zimmerman GA, McIntyre TM, Prescott SM. "Oxidatively Modified LDL Contains Phospholipids With Platelet-Activating Factor-Like Activity And Stimulates The Growth Of Smooth Muscle Cells." *J. Clin. Invest.* 1995; 96: 2322-2330.

Hirschfield GM, Pepys MB. "C-reactive protein and cardiovascular disease: new insights from an old molecule." *Q J Med.* Nov. 2003; 96(11): 793-807.

Hlatky MA. "Evaluation Of Chest Pain In The Emergency Department." *N. Eng. J. Med.* 1997; 337(23): 1687-1689.

Hoff HF, O'Neill J. "Lesion-Derived Low Density Lipoprotein And Oxidized Low Density Lipoprotein Share A Lability For Aggregation, Leading To Enhanced Macrophage Degradation." *Arterioscler. Thromb.* 1991; 11(5): 1209-1222.

Hoff HF, O'Neill J, Chisolm III GM, Cole TB, Quehenberger O, Esterbauer H, Jurgens G. "Modification Of Low Density Lipoprotein With 4-Hydroxynonenal Induces Uptake By Macrophages." *Arteriosclerosis* 1989; 9(4):538-549.

Hoffmeister HM, Jur M, Wendel HP, Heller W, Seipel L. "Alterations Of Coagulation And Fibrinolytic And Kallikrein-Kinin Systems In The Acute And Post-Acute Phases In Patients With Unstable Angina Pectoris." *Circulation* 1995; 91(10): 2520-2527.

Holvoet P, Perez G, Bernar H, Brouwers E, Vanloo B, Rosseneu M, Collen D. "Stimulation With A Monoclonal Antibody (mAb4E4) Of Scavenger Receptor-Mediated Uptake Of Chemically Modified Low Density Lipoproteins By THP-1-Derived Macrophages Enhances Foam Cell Generation." *J. Clin. Invest.* 1994; 93: 89-98.

Holvoet P, Collen D. "Beta-VLDL Hypercholesterolemia Relative To LDL Hypercholesterolemia Is Associated With Higher Levels Of Oxidized Lipoproteins And A More Rapid Progression Of Coronary Atherosclerosis In Rabbits." *Arterioscler. Thromb. Vasc. Biol.* 1997; 17(11): 2376-2382.

Holvoet P, Collen D. "Oxidized Lipoproteins In Atherosclerosis And Thrombosis." *FASEB J.* 1994; 8: 1279-1284.

Holvoet P, Collen D. "Thrombosis And Atherosclerosis." *Curr. Opinion Lipidol.* 1997; 8: 320-328.

Holvoet P, Perez G, Zhao Z, Brouwers E, Bernar H, Collen D. "Malondialdehyde-Modified Low Density Lipoproteins In Patients With Atherosclerotic Disease." *J. Clin. Invest.* 1995; 95: 2611-2619.

Holvoet P, Donck J, Landeloos M, Brouwers E, Luijtens K, Arnout J, Lesaffre E, Vanrenterghem Y, Collen D. "Correlation Between Oxidized Low Density Lipoproteins and Von Willebrand Factor In Chronic Renal Failure." *Thromb. Haemost.* 1996; 76(5): 663-669.

Holvoet P, Van Kleemput J, Collen D, Vanhaecke J. "Correlation Between Oxidized Low Density Lipoproteins And Coronary Artery Disease In Heart Transplant Patients." Abstract Publish in *Final Programme* of 66th Congress of the European Atherosclerosis Society, Florence (Italy), Jul. 13-14, 1996; *Abstract Book*, p. 47.

Holvoet P, Stassen JM, Van Cleemput J, Collen D, Vanhaecke J. "Oxidized Low Density Lipoproteins In Patients With Transplant-Associated Coronary Artery Disease." *Arterioscler. Thromb. Vasc. Biol.* 1998; 18(1): 100-107.

Holvoet P, Theilmeier G, Shivalkar B, Flameng W, Collen D. "LDL Hypercholesterolemia Is Associated With Accumulation Of Oxidized LDL, Atherosclerotic Plaque Growth, And Compensatory Vessel Enlargement In Coronary Arteries Of Miniature Pigs." *Arterioscler. Thromb. Vasc. Biol.* 1998; 18: 415-422.

Holvoet P, Collen D, Vanhaecke J. Presentation at 70th Scientific Session Of The American Heart Association, Orlando, Florida, Nov. 9-12, and published in abstract form in *Circulation* 1997; 96(Suppl. I): I417 (Abstract 2328).

Holvoet P, Vanhaecke J, Janssens S, Van de Werf F, Collen D. "Oxidized LDL And Malondialdehyde-Modified LDL In Patients With Acute Coronary Syndromes And Stable Coronary Artery Disease." *Circulation* 1998; 98: 1487-1494.

Holvoet P, Collen D, Van de Werf F. "Malondialdehyde-Modified LDL As A Marker Of Acute Coronary Syndromes." *J. Am. Med. Assoc.* 1999; 281(18): 1718-1721.

Holvoet P. "Oxidative Modification Of Low-Density Lipoproteins In Atherothrombosis." *Acta Cardiol.* 1998; 53(5): 253-260.

Holvoet P, Mertens A, Verhamme P, Bogaerts K, Beyens G, Verhaeghe R, Collen D, Muls E, Van de Werf F. "Circulating oxidized LDL is a useful marker for identifying patients with coronary artery disease." *Arterioscler Thromb Vasc Biol.* May 2001; 21(5): 844-848.

Holvoet P, Harris TB, Tracy RP, Verhamme P, Newman AB, Rubin SM, Simonsick EM, Colbert LH, Kritchevsky SB. "Association of high coronary heart disease risk status with circulating oxidized LDL in the well-functioning elderly: findings from the Health, Aging, and Body Composition study." *Arterioscler Thromb Vasc Biol.* Aug. 2003; 23(8): 1444-1448.

Hruban RH, Beschorner WE, Baumbgartner WA, Augustine SM, Ren H, Reitz BA, Hutchins GM. "Accelerated Arteriosclerosis In Heart Transplant Recipients Is Associated With A T-Lumphocyte-Mediated Endothelialitis." *Am. J. Pathol.* 1990; 137(4): 871-882.

Hulthe J, Fagerberg B. "Circulating oxidized LDL is associated with subclinical atherosclerosis development and inflammatory cytokines (AIR Study)." *Arterioscler Thromb Vasc Biol.* Jul. 1, 2002; 22(7):1162-1167.

Itabe H, Takeshima E, Iwasaki H, Kimura J, Yoshida Y, Imanaka T, Takano T. "A Monoclonal Antibody Against Oxidized Lipoprotein Recognizes Foam Cells In Atherosclerotic Lesions: Complex Formation Of Oxidized Phosphatidylcholines And Polypeptides." *J. Biol. Chem.* 1994; 269(21): 15274-15279.

Itabe H, Yamamoto H, Imanaka T, Shimamura K, Uchiyama H, Kimura J, Sanaka T, Hata Y, Takano T. "Sensitive Detection Of Oxidatively Modified Low Density Lipoprotein Using A Monoclonal Antibody." *J. Lipid Res.* 1996; 37: 45-53.

Juckett MB, Balla J, Balla G, Jessurun J, Jacob HS, Vercellotti GM. "Ferritin Protects Endothelial Cells From Oxidized Low Density Lipoprotein In Vitro." *Am. J. Pathol.* 1995; 147(3): 782-789.

Kaplan R, Aynedjian HS, Schlondorff D, Bank N. "Renal Vasoconstriction Caused By Short-Term Cholesterol Feeding Is Corrected By Thromboxane Antagonist Or Probucol." *J. Clin. Invest.* 1990; 86: 1707-1714.

Keane WF, Mulcahy WS, Kasiske BL, Kim Y, O'Donnell MP. "Hyperlipidemia And Progressive Renal Disease." *Kidney Int.* 1991; 39(Suppl.): S41-S48.

Kolata, G. "A New Generation Of Tests To Determine Heart Trouble." *New York Times News Service*. 7 pages (Nov. 26, 1995).

Koskinen P, Lemstrom K, Bruggeman C, Lautenschlager I, Hayry P. "Acute Cytomegalovirus Infection Induces a Subendothelial Inflammation (Endothelialitis) In The Allograft Vascular Wall. A Possible Linkage With Enhanced Allograft Arteriosclerosis." *Am. J. Pathol.* 1994; 144(1): 41-50.

Kotani K, Maekawa M, Kanno T, Kondo A, Toda N, Manabe M. "Distribution Of Immunoreactive Malondialdehyde-Modified Low-Density Lipoprotein In Human Serum." *Biochima et Biophysica Acta* 1994; 1215: 121-125.

Lee TH, Goldman L. Serum Enzymes In The Diagnosis Of Acute Myocardial Infarction, *Annals of Internal Medicine* 1986; 105: 221-223.

Libby P. Salomon RN, Payne DD, Schoen FJ, Pober JS. "Functions Of Vascular Wall Cells Related To Development Of Transplantation-Associated Coronary Arteriosclerosis." *Transplant. Proc.* 1989; 21 (4) : 3677-3684.

Lynch SM, Morrow JD, Roberts II LJ, Frei B. "Formation Of Non-Cyclooxygenase-Derived Prostanoids ($F_2$Isoprostanes) In Plasma And Low Density Lipoprotein Exposed To Oxidative Stress In Vitro." *J. Clin. Invest.* 1994; 93: 998-1004.

Mabile L, Fitoussi G, Periquet B, Schmitt A, Salvayre R, Negre-Salvayre A. "Alpha-Tocopherol And Trolox Block The Early Intracellular Events (TBARS And Calcium Rises) Elicited By Oxidized Low Density Lipoproteins In Cultured Endothelial Cells." *Free Radic. Biol. Med.* 1995; 19(2): 177-187.

Major AS, Dove DE, Ishiguro H, Su YR, Brown AM, Liu L, Carter KJ, Linton MF, Fazio S. "Increased Cholesterol Efflux In Apolipoprotein AI (ApoAI)-Producing Macrophages As A Mechanism For Reduced Atherosclerosis In ApoAI( -/- ) ) mice." *Arterioscler Thromb Vasc Biol.* Nov. 2001; 21(11): 1790-1795.

Menschikowski M, Kasper M, Lattke P, Schiering A, Schiefer S, Stockinger H, Jaross W. "Secretory Group II Phospholipase A2 In Human Atherosclerotic Plaques." *Atherosclerosis* 1995; 118: 173-181.

McCully KS. "Chemical Pathology Of Homocysteine. I. Atherogenesis." *Ann. Clin. Lab. Sci.* 1993; 23(6): 477-493.

Morrow JD, Awad JA, Boss HJ, Blair IA, Roberts II LJ. "Non-Cycloogenase-Derived Prostanoids ($F_2$-isoprostanes) Are Formed In Situ On Phospholipids." *Proc. Natl. Acad. Sci. USA* 1992; 89: 10721-10725.

Muldoon MF et al., Ryan J et al., Oltrona L et al., and Liuzzo G et al. Letters and reply by authors. "C-Reactive Protein And Serum Amyloid A Protein In Unstable Angina." *N. Engl. J. Med.* 1995; 332(6): 398-400.

Murugesan G, Chisolm GM, Fox PL. "Oxidized Low Density Lipoprotein Inhibits The Migration Of Aortic Endothelial Cells In Vitro." *J. Cell. Biol.* 1993; 120(4): 1011-1019.

Neff MS, Eiser AR, Slifkin RF, Baum M, Baez A, Gupta S, Amarga E. "Patients Surviving 10 Years Of Hemodialysis." *Am. J. Med.* 1983; 74: 996-1004.

Ohman EM, Armstrong PW, Christenson RH, Granger CB, Katus HA, Hamm CW, O'Hanesian MA, Wagner GS, Kleiman NS, Harrell Jr. FE, Califf RM, Topol EJ. "Cardiac Troponin T Levels For Risk Stratification In Acute Myocardial Ischemia." *N. Eng. J. Med.* 1996 335(18): 1333-1341.

O'Marcaigh AS, Jacobson RM. "Estimating The Predictive Value Of A Diagnostic Test. How To Prevent Misleading Or Confusing Results." *Clin. Ped.* 1993; 32(8): 485-491.

Palinski W, Rosenfeld ME, Ylä-Herttuala S, Gurtner GC, Socher SS, Butler SW, Parthasarathy S, Carew TE, Steinberg D, Witztum JL. "Low Density Lipoprotein Undergoes Oxidative Modification In Vivo." *Proc. Natl. Acad. Sci. USA* 1989; 86: 1372-1376.

Palinski W, Yla-Herttuala S, Rosenfeld ME, Butler SW, Socher SA, Parthasarathy S, Curtiss LK, Witztum JL. "Antisera And Monoclonal Antibodies Specific For Epitopes Generated During Oxidative Modification Of Low Density Lipoprotein." *Arteriosclerosis* 1990; 10(3): 325-335.

Parthasarathy S, Wieland E, Steinberg D. "A Role For Endothelial Cell Lipoxygenase In The Oxidative Modification Of Low Density Lipoprotein." *Proc. Nat. Acad. Sci. USA* 1989; 86: 1046-1050.

Penn MS, Chisolm GM. "Oxidized lipoproteins, altered cell function and atherosclerosis." *Atherosclerosis* 1994; 108(Suppl.): S21-S29.

Pocock SJ. *Clinical Trials. A Practical Approach.* Chapter 14: "Further Aspects of Data Analysis." pp. 211-233. John Wiley & Sons. 1993.

Rasmussen O, Thomsen C, Ingerslev J, Hermansen K. "Decrease Of Von Willebrand Factor Levels After A High-Monounsaturated Fat Diet In Non-Insulin-Dependent Diabetic Subjects." *Metabolism* 1994; 43(11): 1406-1409.

Ravalli S, Marboe CC, D'Agati VD, Michler RE, Sigal E, Cannon PJ. "Immunohistochemical Demonstration Of 15-Lipoxygenase In Transplant Coronary Artery Disease." *Arterioscler. Thromb. Vasc. Biol.* 1995; 15(3): 340-348.

Reade V, Tailleux A, Reade R, Harduin P, Cachera C, Tacquet A, Fruchart JC, Fievet C. "Expression Of Apolipoprotein B Epitopes In Low Density Lipoproteins Of Hemodialyzed Patients." *Kidney Int.* 1993; 44: 1360-1365.

Reverter JC, Escolar G, Sanz C, Cases A, Villamor N, Nieuwenhuis HK, Lopez J, Ordinas A. "Platelet Activation During Hemodialysis Measured Through Exposure Of P-Selectin: Analysis By Flow Cytometric And Ultrastructural Techniques." *J. Lab. Clin. Med.* 1994; 124(1): 79-85.

Ridker PM, Glynn, RJ, Hennekens, CH. "C-Reactive Protein Adds To The Predictive Value Of Total And HDL Cholesterol In Determining Risk Of First Myocardial Infarction." *Circulation* 1998; 97:2007-2011.

Ridker PM, Buring JE, Shih J, Matias M, Hennekens CH. "Prospective Study Of C-Reactive Protein And The Risk Of Future Cardiovascular Events In Stable And Unstable Angina." *Circulation* 1998; 98:731-733.

Rose EA, Smith CR, Petrossian GA, Barr ML, Reemtsma K. "Humoral Immune Responses After Cardiac Transplantation: Correlation With Fatal Rejection And Graft Atherosclerosis." *Surgery* 1989; 106 (2) : 203-208.

Rosenfeld ME, Palinski W, Yla-Herttuala, Butler S, Witztum JL. "Distribution Of Oxidation Specific Lipid-Protein Adducts And Apolipoprotein B In Atherosclerotic Lesions Of Varying Severity From WHHL Rabbits." *Arteriosclerosis* 1990; 10 (3) : 336-349.

Ross R. "The Pathogenesis Of Atherosclerosis: A Perspective For The 1990s." *Nature* 1993; 362: 801-809.

Salonen JT, Yla-Herttuala S, Yamamoto R, Butler S, Korpela H, Salonen R, Nyyssonen K, Palinski W, Witztum JL. "Autoantibody Against Oxidised LDL And Progression Of Carotid Atherosclerosis." *Lancet* 1992; 339(8798): 883-887.

Sasavage N. "Predicting Coronary Artery Disease. New Markers Could Identify Patients At Risk." *Clin. Lab. News* Mar. 1998; pp. 6-7.

Savenkova ML, Mueller DM, Heinecke JW. "Tyrosyl Radical Generated By Myeloperoxidase Is A Physiological Catalyst For The Initiation Of Lipid Peroxidation In Low Density Lipoprotein." *J. Biol. Chem.* 1994; 269(32): 20394-20400.

Schaffner T, Taylor K, Bartucci EJ, Fischer-Dzoga K, Beeson JH, Glagov S. Wissler RW, "Arterial Foam Cells With Distinctive Immunomorphologic And Histochemical Features Of Macrophages." *Am. J. Pathol.* 1980; 100(1): 57-80.

Schonbeck U, Gerdes N, Varo N, Reynolds RS, Horton DB, Bavendiek U, Robbie L, Ganz P, Kinlay S, Libby P. "Oxidized Low-Density Lipoprotein Augments And 3-Hydroxy-3-Methylglutaryl Coenzyme A Reductase Inhibitors Limit CD40 And CD40l Expression In Human Vascular Cells." *Circulation* 2002; 106(23): 2888-2893.

Shacter E. "Quantification And Significance Of Protein Oxidation In Biological Samples." *Drug Metab Rev.* Aug.-Nov. 2000 ; 32(3-4): 307-26.

Shultz EK. "Clinical Interpretation Of Laboratory Procedures." Chapter 14 in *Teitz, Fundamentals of Clinical Chemistry*. Burtis CA, Ashwood ER (eds.). 4th edition 1996. W.B.Saunders Company. pp. 192-199.

Schulz T, Schiffl H, Scheithe R, Hrboticky N, Lorenz R. "Preserved Antioxidative Defense Of Lipoproteins In Renal Failure And During Hemodialysis." *Am. J. Kidney Dis.* 1995; 25(4): 564-571.

Selwyn AP, Kinlay S, Libby P, Ganz P. "Atherogenic Lipids, Vascular Dysfunction, And Clinical Signs Of Ischemic Heart Disease." *Circulation* 1997; 95(1): 5-7.

Sparrow CP, Olszewski J. "Cellular Oxidative Modification Of Low Density Lipoprotein Does Not Require Lipoxygenases." *Proc. Nat. Acad. Sci. USA* 1992; 89: 128-131.

Sparrow CP, Partharasathy S, Leake DS, Steinberg D. "Enzymatic Modification Of Low Density Lipoprotein By Purified Lipoxygenase Plus Phospholipase-$A_2$ Mimic Cell-Mediated Oxidative Modification." *J. Lipid Res.* 1988; 29: 745-753.

Steinberg D, Witztum JL. "Lipoproteins And Atherogenesis: Current Concepts." *J. Am. Med. Assoc.* 1990; 264(23): 3047-3052.

Steinberg D. "Clinical Trials Of Antioxidants In Atherosclerosis: Are We Doing The Right Thing?" *Lancet* 1995; 346: 36-38.

Steinberg D. "Lewis A. Conner Memorial Lecture. Oxidative Modification Of LDL And Atherogenesis." *Circulation* 1997; 95: 1062-1071.

Steinbrecher UP, Parthasarathy S, Leake DS, Witztum JL, Steinberg D. "Modification Of Low Density Lipoprotein By Endothelial Cells Involves Lipid Peroxidation And Degradation Of Low Density Lipoprotein Phospholipids." *Proc. Nat. Acad. Sci. USA* 1984; 81: 3883-3887.

Steinbrecher UP. "Oxidation Of Low Density Lipoprotein Results In Derivatization Of Lysine Residues Of Apolipoprotein B By Lipid Peroxide Decomposition Products." *J. Biol. Chem.* 1987; 262(8): 3603-3608.

Steinbrecher UP, Lougheed M. "Scavenger Receptor-Independent Stimulation Of Cholesterol Esterification In Macrophages By Low Density Lipoprotein Extracted From Human Aortic Intima." *Arterioscler. Thromb.* 1992; 12(5): 608-625.

Sutherland WH, Walker RJ, Ball MJ, Stapley SA, Robertson MC. "Oxidation Of Low Density Lipoproteins From Patients With Renal Failure Or Renal Transplants." *Kidney Int.* 1995; 48: 227-236.

Tamai O, Matsuoka H, Itabe H, Wada Y, Kohno K, Imaizumi T. "Single LDL Apheresis Improves Endothelium-Dependent Vasodilation In Hypercholesterolemic Humans." *Circulation* 1997; 95(1): 76-82.

Tanaka H, Sukhova GK, Swanson SJ, Cybulsky MI, Schoen FJ, Libby P. "Endothelial And Smooth Muscle Cells Express Leukocyte Adhesion Molecules Heterogeneously During Acute Rejection Of Rabbit Cardiac Allografts." *Am. J. Pathol.* 1994; 144(5): 938-951.

Trachtman H, Schwob N, Maesaka J, Valderrama E. "Dietary Vitamin E Supplementation Ameliorates Renal Injury In Chronic Puromycin Aminonucleoside Nephropathy." *J. Am. Soc. Nephrol.* 1995; 5(10): 1811-1819.

Tuzcu EM, Hobbs RE, Rincon G, Bott-Silverman C, De Franco AC, Robinson K, McCarthy PM, Stewart RW, Guyer S, Nissen SE. "Occult And Frequent Transmission Of Atherosclerotic Coronary Disease With Cardiac Transplantation. Insights From Intravascular Ultrasound." *Circulation* 1995; 91(6): 1706-1713.

Uchida K, Kanematsu M, Sakai K, Matsuda T, Hattori N, Mizuno Y, Suzuki D, Miyata T, Noguchi N, Niki E, Osawa T. "Protein-Bound Acrolein: Potential Markers For Oxidative Stress." *Proc. Natl. Acad. Sci. USA* 1998; 95: 4882-4887.

Van de Werf F. "Cardiac Troponins In Acute Coronary Syndromes." *N. Eng. J. Med.* 1996; 335(18): 1388-1389.

Varo N, de Lemos JA, Libby P, Morrow DA, Murphy SA, Nuzzo R, Gibson CM, Cannon CP, Braunwald E, Schonbeck U. "Soluble CD40L: Risk Prediction After Acute Coronary Syndromes." *Circulation* 2003; 108(9): 1049-1052.

Wentworth P Jr, Nieva J, Takeuchi C, Galve R, Wentworth AD, Dilley RB, DeLaria GA, Saven A, Babior BM, Janda KD, Eschenmoser A, Lerner RA. "Evidence for ozone formation in human artherosclerotic arteries." *Science* 2003; 302 (5647): 1053-1056.

Ylä-Herttuala S, Palinski W, Rosenfeld ME, Parthasarathy S, Carew TE, Butler S, Witztum JL, Steinberg D. "Evidence For The Presence Of Oxidatively Modified Low Density Lipoprotein In Atherosclerotic Lesions Of Rabbit And Man." *J. Clin. Invest.* Oct. 1989; 84: 1086-1095.

Zaidi S, Pandey RN, Kidwai AM, Murti CRK. "A Rapid Method For Preparation Of Sarcolemma From Frog Leg Skeletal Muscle." *Chemical Abstracts* Jun. 7, 1982; 96(23): 196091e.

Zawadzki Z, Milne RW, Marcel YL. "An Immunochemical Marker Of Low Density Lipoprotein Oxidation." *J. Lipid Res.* 1989; 30: 885-891.

Zhao B, Dierichs R, Harrach-Ruprecht B, Winterhorff H. "Oxidized LDL Induces Serotonin Release From Blood Platelets." *Am. J. Hematol.* 1995; 48: 285-287.

Zwaginga JJ, Koomans HA, Sixma JJ, Rabelink TJ. "Thrombus Formation And Platelet-Vessel Wall Interaction In The Nephrotic Syndrome Under Flow Conditions." *J. Clin. Invest.* 1994; 93: 204-211.

Zweig MH, Broste SK, Reinhart RA. "ROC Curve Analysis: An Example Showing The Relationships Among Serum Lipid And Apolipoprotein Concentrations In Identifying Patients With Coronary Artery Disease." *Clin. Chem.* 1992; 38 (8) : 1425-1428.

Holvoet P, Kritchevsky SB, Tracy RP, Mertens A, Rubin SM, Butler J, Goodpaster B, Harris TB. "The Metabolic Syndrome, Circulating Oxidized LDL, And Risk of Myocardial Infarction In Well-Functioning Elderly People In The Health, Aging, And Body Composition Cohort." *Diabetes.* 2004; 53(4): 1068-1073.

Sigurdardottir V, Fagerberg B, Hulthe J. "Circulating Oxidized Low-Density Lipoprotein (LDL) Is Associated With Risk Factors of The Metabolic Syndrome And LDL Size in Clinically Healthy 58-Year-Old Men (AIR Study)." *J Intern Med.* 2002; 252(5): 440-447.

Holvoet P. "Oxidized LDL And Coronary Heart Disease," *Acta Cardiol.* Oct. 2004; 59(5): 479-484.

Cesari M, Kritchevsky SB, Nicklas BJ, Penninx BW, Holvoet P, Koh-Banerjee P, Cummings SR, Harris TB, Newman AB, Pahor M, "Lipoprotein peroxidation and mobility limitation: results from the health, aging, and body composition study," *Arch Intern Med.* Oct. 10, 2005; 165(18): 2148-2154.

Meisinger C, Baumert J, Khuseyinova N, Loewel H, Koenig W. "Plasma oxidized low-density lipoprotein, a strong predictor for acute coronary heart disease events in apparently healthy, middle-aged men from the general population," *Circulation.* Aug. 2, 2005; 112(5): 651-657 (Epub Jul. 25, 2005).

Mercodia AB. "Triple-Marker Test"; 4-page brochure (photocopied onto 2 sheets); Nov. 2004.

Johnston N, Jemberg T, Langerqvist B, Siegbahn A, Wallentin L. "Improved Identification Of Patents With Coronary Artery Disease By The Use Of New Lipid And Lipoprotein Biomarkers," *Am J Cardiol.* Mar. 1, 2006; 97(5): 640-645; Epub Jan. 10, 2006.

Johnston N, Jemberg T, Langerqvist B, Siegbahn A, Wallentin L. "Oxidized Low-Density Lipoprotein As A Predictor Of Outcome In Patients With Unstable Coronary Artery Disease," *Int J Cardiol.* (not yet in print); Epub ahead of print Dec. 7, 2005.

Griffin ME, McInerney D, Fraser A, Johnson AH, Collins PB, Owens D, Tomkin GH. "Autoantibodies to Oxidized Low Density Lipoprotein: the Relationship to Low Density Lipoprotein Fatty Acid Composition in Diabetes." *Diabetic Medicine* (1997), vol. 14, pp. 741-747.

Liu K, Cuddy TE, Pierce GN. "Oxidative status of lipoproteins in coronary disease patients." *American Heart Journal* (1992), vol. 123, pp. 285-290.

Palinski W, Horkko S, Miller E, Steinbrecher UP, Powell HC, Curtiss LK, Witztum JL. "Cloning of Monoclonal Autoantibodies to Epitopes of Oxidized Lipoproteins from Apolipoprotein E-deficient Mice." *Journal of Clinical Investigation* (1996), vol. 98, pp. 800-814.

Schier R, McCall A, Adams GP, Marshall KW, Merritt H, Yim M, Crawford RS, Weiner LM, Marks C, Marks JD. "Isolation of Picomolar Affinity Anti-c-erbB-2 Single-chain Fv by Molecular Evolution of the Complementary Determining Regions in the Center of the Antibody Binding Site." *Journal of Molecular Biology* (1996), vol. 263, pp. 551-567.

Winzor DJ, De Jersey J. "Biospecific Interactions: Their Quantitative Characterization And Use For Solute Purification." *Journal of Chromatography* (1989), vol. 492, pp. 377-430.

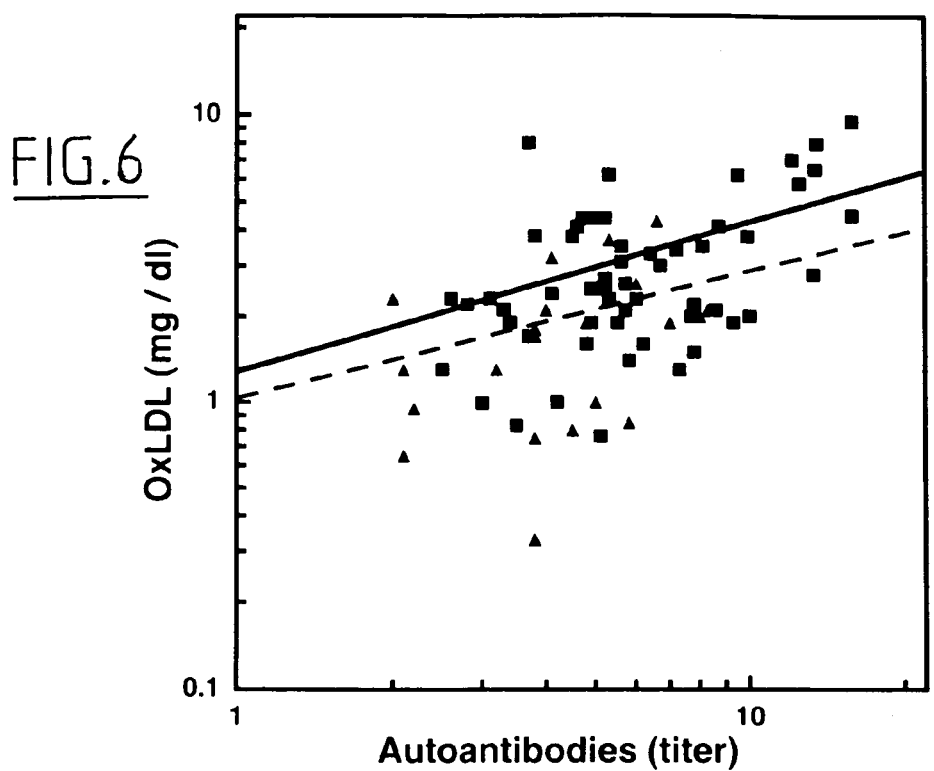
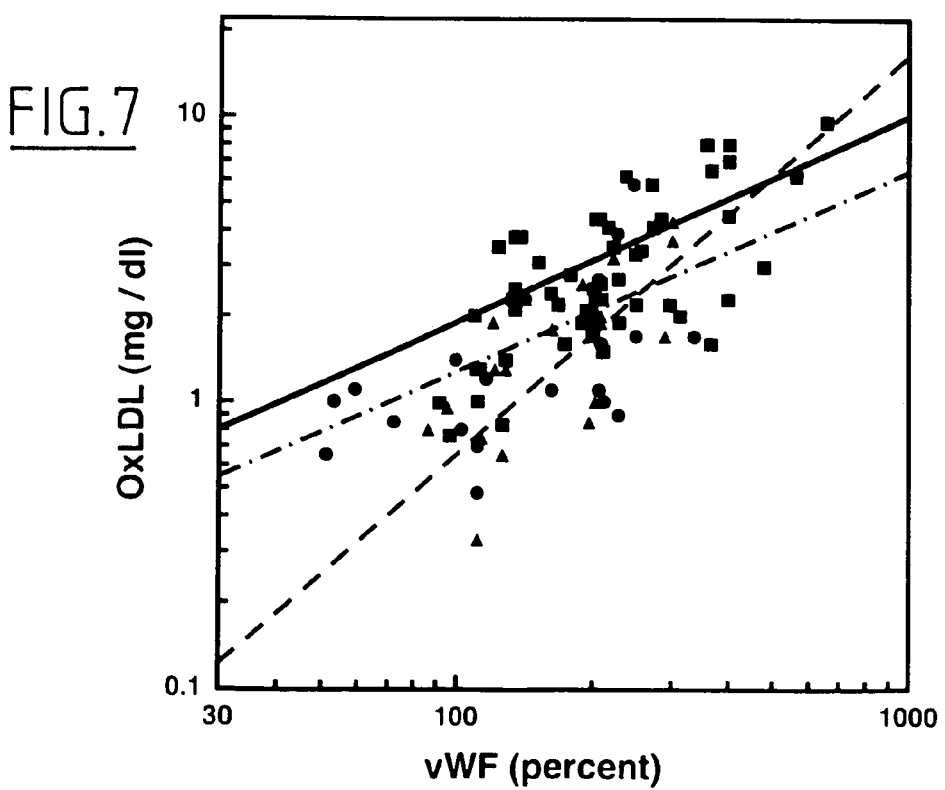

ASSAYS, ANTIBODIES, AND STANDARDS FOR DETECTION OF OXIDIZED AND MDA-MODIFIED LOW DENSITY LIPOPROTEINS

RELATED APPLICATIONS

This application is a divisional of U.S. patent application Ser. No. 09/446,259, filed Dec. 20, 1999, now U.S. Pat. No. 6,727,102, which is the national stage in the United States of International Application No. PCT/EP97/03493, filed Jul. 1, 1997, which claims priority to PCT/EP97/03287, filed Jun. 20, 1997. All priority rights under 35 U.S.C. §§ 119 and 120 to and for those applications and the present application are hereby claimed.

BACKGROUND

The present invention relates to assays, antibodies (particularly monoclonal antibodies), and standards for detection (i.e., determination of the presence and/or quantitation of the amount) of oxidized low density lipoprotein (OxLDL) and malondialdehyde-modified low density lipoprotein (MDA-modified LDL) in samples, the samples typically being derived from body fluids or tissues.

Lipoproteins are multicomponent complexes of protein and lipids. Each type of lipoprotein has a characteristic molecular weight, size, chemical composition, density, and physical role. The protein and lipid are held together by noncovalent forces.

Lipoproteins can be classified on the basis of their density as determined by ultracentrifugation. Thus, four classes of lipoproteins can be distinguished: High Density Lipoproteins (HDL), Intermediate Density Lipoproteins (IDL), Low Density Lipoproteins (LDL), and Very Low Density Lipoproteins (VLDL).

The purified protein components of a lipoprotein particle are called apolipoproteins (apo). Each type of lipoprotein has a characteristic apolipoprotein composition. In LDL the prominent apolipoprotein protein is apo B-100. Apo B-100 is one of the longest single chain polypeptides known and consists of 4536 amino acids. Of these amino acids the lysine residues or moieties (there are 356 such lysine residues or moieties) can be substituted or modified by aldehydes (e.g., malondialdehyde).

Oxidation of the lipids in LDL (whether in vitro, e.g., by copper-induced oxidation, or whether in vivo) results in the generation of reactive aldehydes, which can then interact with the lysine residues or moieties of apo B-100. The outcome of this lysine substitution or modification is that the resulting OxLDL, which is also MDA-modified LDL, is no longer recognized by the LDL receptor at the surface of fibroblasts but by scavenger receptors at the surface of macrophages. At least 60 out of the 356 lysines (or lysine residues or moieties) of apo B-100 have to be substituted in order to be recognized by the scavenger receptors (see document number 1 of the documents listed near the end of this application, all of which documents are hereby incorporated in their entireties for all purposes). The uptake of such OxLDL by macrophages results in foam cell generation, which is considered to be an initial step in atherosclerosis.

Endothelial cells under oxidative stress (e.g., in acute myocardial infarction patients) and activated blood platelets also produce aldehydes, which interact with the lysine moieties in apo B-100, resulting in the generation of aldehyde-modified LDL that is also recognized by the scavenger receptors. However, the lipids in this aldehyde-modified LDL are not oxidized. Enzymatic activity in macrophages (e.g. myeloperoxidase) results in the oxidation of both the lipid and the protein moieties of LDL. All these pathways result in aldehyde-type modification of the protein moiety of LDL.

In vitro experiments and experiments in animal models have suggested that OxLDL and/or aldehyde-modified LDL may contribute to the progression of atherosclerosis by inducing endothelial dysfunction, foam cell generation, smooth muscle cell proliferation, and platelet activation (for review see document number 2). A positive correlation between the levels of autoimmune antibodies that cross-react with aldehyde-modified LDL and the progression of carotid atherosclerotic lesions in patients suggested that OxLDL and/or aldehyde-modified LDL might contribute to the progression of human atherosclerosis (see document 3).

However, the possibility that the autoimmune antibodies were directed against other aldehyde-modified proteins, e.g., albumin, could not be excluded. Therefore, the contribution of OxLDL and aldehyde-modified LDL (whether or not resulting from oxidation of the lipid moiety) to human atherosclerosis may be able to be established when non-invasive tests that are specific for these substances (i.e., have high affinity for those substances in preference to other substances) become available.

Because the underlying mechanisms of oxidation of LDL may be different in different patient populations (e.g., in diabetes patients, chronic renal failure patients, heart transplant patients) and because at least some of the mechanisms may be independent of lipid oxidation, such tests should be specific for both OxLDL and aldehyde-modified LDL (e.g., MDA-modified LDL) and thus preferentially be based on the detection of conformational changes that specifically occur in the apo B-100 moiety of LDL following aldehyde-type substitution of lysine residues. In other words, there is a need for such non-invasive tests (i.e., assays) that are highly specific for the analytes of interest (i.e., MDA-modified LDL and OxLDL). There is also a need for antibodies that are specific for the analytes of interest. There is also a need for a stable standard (e.g., to be used as calibrator and/or control) for the assays.

SUMMARY OF THE INVENTION

An invention satisfying those needs and having other features and advantages that will be apparent to those skilled in the art has now been developed. The present invention provides antibody-based assays that are capable of specifically quantitating (quantifying) both OxLDL and aldehyde-modified LDL or MDA-modified LDL in samples, e.g., samples derived from body fluids (like plasma or serum) or tissues. The present invention also provides monoclonal antibodies useful in those assays and cell lines (hybridomas) that produce those antibodies. The present invention also provides a storage-stable standard, which can be used as a calibrator and as a control for the assays. Having such a standard is necessary for having reliable and reproducible and therefore useful assays.

Broadly, in one aspect the present invention concerns an immunological assay for the detection and/or quantification of MDA-modified LDL and OxLDL in a sample, said assay comprising:

a) contacting the sample with a first antibody that has high affinity for MDA-modified LDL and OxLDL; and b) thereafter visualizing and/or quantifying a binding reaction between the first antibody and the MDA-modified LDL and OxLDL present in the sample;

wherein the MDA-modified LDL and OxLDL for which the first antibody has high affinity contain at least 60 substituted lysine moieties per apo B-100 moiety.

That assay may, for example, be a competitive. assay, a sandwich assay, an immunohistochemical assay, etc. "Competitive assays" are well-known and any competitive assay may be used in this invention provided it is within the limitations of the invention and that the benefits of the invention can be achieved. "Sandwich assays" are well-known and any sandwich assay may be used in this invention provided it is within the limitations of the invention and that the benefits of the invention can be achieved. "Immunohistochemical assays" are well-known and any immunohistochemical assay may be used in this invention provided it is within the limitations of the invention and that the benefits of the invention can be achieved.

In another aspect, the present invention concerns an immunological sandwich assay for the detection and/or quantification of MDA-modified LDL in a sample in which assay a first antibody that has a high affinity for MDA-modified LDL is bound to a substrate, said assay comprising:

(a) contacting the sample with the substrate having bound to it the first antibody under binding conditions so that at least some of any MDA-modified LDL in the sample will bind to the first antibody;

(b) thereafter removing unbound sample from the substrate;

(c) thereafter contacting the substrate with a second antibody that has a high affinity for MDA-modified LDL; and (d) thereafter visualizing and/or quantifying the MDA-modified LDL that was present in the sample;

wherein the MDA-modified LDL for which the first antibody and the second antibody have high affinity contains at least 60 substituted lysine moieties per apo B-100 moiety.

As used herein (including the claims), "high affinity" means an affinity constant (association constant) of at least about $5 \times 10^8$ M$^{-1}$, desirably at least about $1 \times 10^9$ M$^{-1}$, preferably at least about $1 \times 10^{10}$ M$^{-1}$, and most preferably of at least about $1 \times 10^{11}$ M$^{-1}$. As used herein (including the claims), "low affinity" means an affinity constant (association constant) of less than about $1 \times 10^7$ M$^{-1}$, desirably less than about $1 \times 10^6$ M$^{-1}$, and preferably less than about $1 \times 10^5$ M$^{-1}$. Affinity constants are determined in accordance with the appropriate method described in Holvoet et al. (4).

The antibodies that can be used in this invention will bind with MDA-modified LDL and/or OxLDL whose apo B-100 moieties contain at least 60, desirably at least about 90, more desirably at least about 120, preferably at least about 180, more preferably at least about 210, and most preferably at least about 240 substituted lysine residues per apo B-100 moiety. The range of lysine substitution will generally be from 60 to about 240 and preferably from about 120 to about 240 substituted lysine moieties per apo B-100 moiety.

Each new monoclonal antibody is highly specific for a conformational epitope that is present when at least about 60, preferably at least about 120 lysine residues, are substituted and by virtue thereof can distinguish various markers or indications related to atherosclerosis. Antibodies recognizing epitopes present when less than about 60 lysines are substituted or modified are less specific but are still useful (e.g., they may be used as the secondary antibody in a sandwich ELISA).

The preferred antibodies used herein are monoclonal antibodies mAb-4E6, mAb-1h11, and mAb-8A2. Their affinity constants for native LDL, MDA-modified LDL, and OxLDL are as follows:

| Antibody | Native LDL | MDA-modified LDL | OxLDL |
| --- | --- | --- | --- |
| mAb-4E6 | less than $1 \times 10^6$ | $3 \times 10^{10}$ | $2 \times 10^{10}$ |
| mAb-1H11 | less than $1 \times 10^6$ | $3 \times 10^{10}$ | less than $1 \times 10^6$ |
| mAb-8A2 | $5 \times 10^9$ | $1 \times 10^{10}$ | $1 \times 10^{10}$ |

In yet another aspect, the present invention concerns (a) monoclonal antibody mAb-4E6 produced by hybridoma Hyb4E6 deposited at the BCCM under deposit accession number LMBP 1660 CB on Apr. 24, 1997, (b) monoclonal antibody mAb-8A2 produced by hybridoma Hyb8A2 deposited at the BCCM under deposit accession number LMBP 1661 CB on Apr. 24, 1997, (c) hybridoma Hyb4E6 deposited at the BCCM under deposit accession number LMBP 1660 CB on Apr. 24, 1997, and (d) hybridoma Hyb8A2 deposited at the BCCM under deposit accession number LMBP 1661 CB on Apr. 24, 1997.

The antibodies used in the assays of this invention are preferably those two (i.e., mAb-4E6 and mAb-8A2) as well as mAb-1H11. The cell line for antibody mAb-1H11 is produced by hybridoma Hyb1H11, which was deposited at the BCCM under deposit accession number LMBP 1659 CB on Apr. 24, 1997.

The BCCM is the Belgian Coordinated Collections of Microorganisms authorized by the "Budapest Treaty of 28 Apr. 1977 on the International Recognition of the Deposit of Microorganisms for the Purposes of Patent Procedure." Its address Belgian Coordinated Collections of Microorganisms (BCCM), Prime Minister's Services, Federal Office for Scientific, Technical and Cultural Affairs (OSTC), Rue de la Science 8, B-1000 Brussels, Belgium. In accordance with The United States Code Of Federal Regulations ("CFR") (e.g., 37 CFR § 1.808) and The United States Patent And Trademark Offices's Manual Of Patent Examination ("MPEP") (e.g., § 2410.01), all restrictions on the avaliability to the public of the deposited material (except as permitted by the CFR and MPEP) will be irrevocably removed upon the granting of any patent issuing from this application or from any related application, including any parent application (see "Related Applications," above). Futhermore, each of the deposits will be replaced if a viable sample of it cannot be furnished by the BCCM.

The assay may be of a type that is well-known, such as an Enzyme-Linked Immunosorbent Assay (ELISA). For example, in the case of a sandwich ELISA, mAb-4E6 (for MDA-modified LDL and OxLDL) or mAb-1H11 (for MDA-modified LDL) may be bound to a solid substrate and subsequently contacted with a sample to be assayed. After removal of the sample, binding between the specific antibody and OxLDL and/or MDA-modified LDL captured out of the sample can be visualized and/or quantified by detection means. Detection means may be a labeled, less specific secondary antibody that recognizes a different part of the apo B-100 moiety of the captured analyte (e.g., mAb-8A2).

In the case of a competitive ELISA, a solid substrate coated with OxLDL or MDA-modified LDL may be contacted for a predetermined period of time with the monoclonal antibody mAb-4E6 and a sample thought or known to contain OxLDL and/or MDA-modified LDL, after which period of time unbound antibody and sample are removed and a binding reaction between antibody and OxLDL and/or MDA-modified LDL bound to the substrate is visualized and/or quantified. Quantification in a competitive ELISA is indirect because the binding between the antibody and the analyte in the sample is not measured but instead the amount of antibody that binds to the known amount of OxLDL or MDA-modified LDL that is coated on (bound to) the substrate is measured. The more antibody bound to the known amount of OxLDL or MDA-modified LDL coated on the substrate, the less analyte there was in the sample.

In yet another aspect, the present invention concerns a stable standard containing MDA-modified LDL whose extent of substitution of its lysine moieties will remain essentially constant over normal periods of time during normal storage for biological materials, the MDA-modified LDL of said standard being made by contacting (incubating) malondialdehyde with LDL at a predetermined molar ratio of malondialdehyde to the apo B-100 moiety of the LDL.

"Over normal periods of time during normal storage for biological materials" as used herein refers to the time periods and conditions under which biological materials to be used in assays and other laboratory work are typically stored. Those conditions will typically include low temperature and in appropriate cases freezing, either with or without lyophilization. Depending on the particular biological material, if the material is stored under the appropriate temperature and other conditions (e.g., lack of vibration or other movement, proper humidity), the material may be stable for at least three months, desirably for over a year, preferably for over two years, and most preferably for over three years.

The standard preferably contains an agent that reduces the ability of any metal ions present to catalyze oxidation of the LDL (e.g., a chelating agent, such as EDTA) and/or one or more anti-oxidants (e.g., BHT and/or Vitamin E). Preferably both the agent that reduces the ability of any metal ions present to catalyze oxidation of the LDL and the anti-oxidant are used. It has surprisingly been found that when using an antibody that is specific for both OxLDL and MDA-modified LDL, the storage-stable standard of this invention (containing MDA-modified LDL and not OxLDL) can be used. That eliminates the need to try to formulate, store, and use a stable standard containing OxLDL. OxLDL may continue to oxidize under typical storage conditions, making using as a standard a composition containing OxLDL difficult if not almost impossible. EDTA will typically be used in concentrations of 0.5 to 5 mM, preferably in concentrations of 0.5 to 2 mM. BHT will typically be used in concentrations of 5 to 50 µM, preferably in concentrations of 10 to 20 µM. Vitamin E will typically be used in concentrations of 5 to 50 µM, preferably in concentrations of 10 to 20 µM. The standard may also contain anti-platelet agents and coagulation inhibitors.

It has been found that LDL that has been modified by treatment with MDA is highly stable. Such MDA-modified LDL (which is not oxidized, i.e., its lipid moiety is not oxidized) could be added to reference plasma samples and those samples could be frozen and thawed without increasing the extent of lysine substitution. Because the total number of lysine residues in all apo B-100 molecules is identical, a constant MDA/apo B-100 molar ratio in the reaction mixture will result in an identical number of substituted lysines in the MDA-modified LDL. In contrast, for example, metal-ion mediated oxidation of LDL ultimately results in a variable extent of lysine substitution because it depends on the oxidation sensitivity of the LDL preparation, which by itself depends on fatty acid composition and antioxidant content, which are highly variable even in healthy control individuals.

As described below, a correlation between the oxidation of LDL and the extent of post-transplant atherosclerosis in heart transplant patients was established using this invention. The relationship between endothelial injury and the modification of LDL was established in chronic renal failure patients that are at high risk for atherosclerotic cardiovascular disease. It was also demonstrated that endothelial injury is an initial step in atherosclerosis.

Based on the characteristics of the oxidatively modified LDL from the plasma of heart transplant and chronic renal failure patients, it was concluded that cell-mediated aldehyde modification independent of lipid oxidation was at least partially involved. This finding further supported the hypothesis that an assay for oxidatively modified LDL has to detect both OxLDL and aldehyde-modified LDL.

In yet another aspect, the invention concerns a kit for conducting a sandwich assay for the determination of OxLDL or MDA-modified LDL or both in a sample, said kit comprising a substrate on which is bound a first antibody that has high affinity for OxLDL or MDA-modified LDL or both, the OxLDL and MDA-modified LDL each having at least 60 substituted lysine moieties per apo B-100 moiety, and a labeled antibody having a high affinity for OxLDL that becomes bound to the first antibody during the assay or for MDA-modified LDL that becomes bound to the first antibody during the assay or for both that become bound to the first antibody during the assay. Preferably the kit further comprises a reactive substance for reaction with the labeled antibody (e.g., an enzyme) to give an indication of the presence of the labeled antibody. Preferably the kit also comprises the stable standards, e.g., in the form of stable calibrators and/or stable controls. Thus, e.g., the bound antibody may be mAb-4E6 or mAb-1H11 and the labeled antibody may be mab-8A2.

BRIEF DESCRIPTION OF THE DRAWINGS

The accompanying drawings are provided to help further describe the invention, which drawings are as follows:

FIG. 6 illustrates the correlation between plasma levels of OxLDL and aldehyde-modified LDL and titers of specific autoantibodies.

FIG. 7 illustrates the correlation between plasma levels of OxLDL and aldehyde-modified LDL and of von Willebrand factor antigen.

Figure 1:
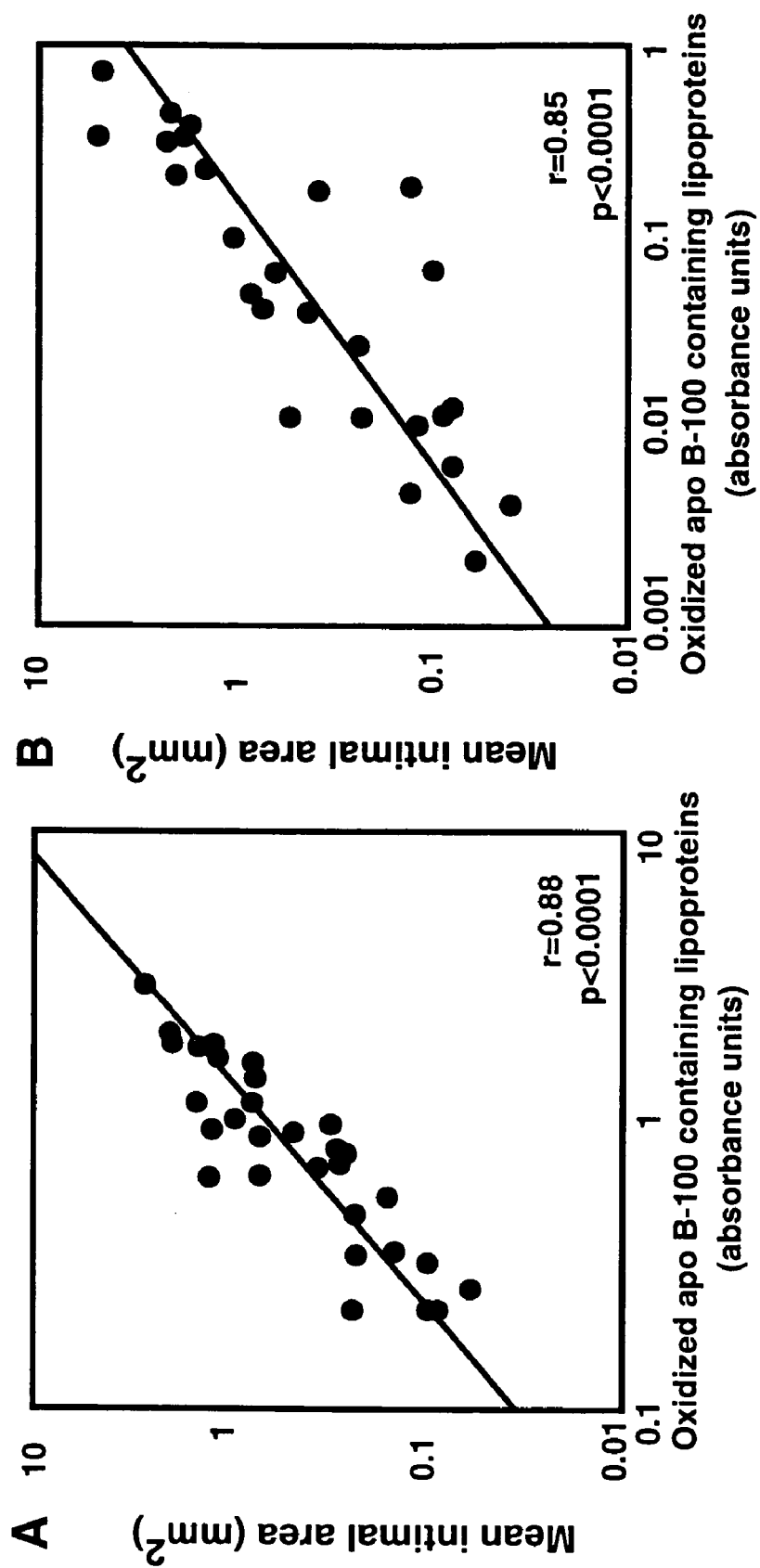
FIG. 1 illustrates the correlation between amounts of oxidized and MDA-modified LDL in coronary lesions in Watanabe heritable hyperlipidemic rabbits (A) and in miniature pigs (B).

These drawings are provided for illustrative purposes only and should not be used to unduly limit the invention.

DETAILED DESCRIPTION OF THE INVENTION

The present invention will be further described in conjunction with the following examples, which are for illustrative purposes and which should not be used to unduly limit the invention.

EXAMPLES

Example 1

Preparation and Characterization of Antibodies Specific for OxLDL and for Aldehyde-modified LDL Balb/c mice were immunized by intravenous and intraperitoneal injection of either OxLDL or MDA-modified LDL. OxLDL was obtained by in vitro incubation of LDL (final apo B-100 concentration 700 µg/ml) with copper chloride (final concentration 640 µM) for 16 h at 37° C. MDA-modified LDL was prepared by incubation of LDL (final apo B-100 concentration 700 µg/ml) with a 0.25 M MDA-solution for 3 h at 37° C. The numbers of substituted lysines, measured in the TBARS assay, was typically 210 per apo B-100 molecule for OxLDL and 240 for MDA-modified LDL. Hybridomas were obtained by PEG induced fusion of spleen lymphocytes derived from immunized mice with P3-X63/Ag-6.5.3 myeloma cells according to standard techniques (4). The screening for hybridomas producing specific antibodies was performed with ELISA using microtiter plates coated with malondialdehyde-modified LDL or copper-oxidized LDL. 308 hybridomas were obtained after immunization of mice with either OxLDL (211) or MDA-modified LDL (97). Hyb4E6 produced antibodies specific for both malondialdehyde-modified and copper-oxidized LDL (mAb-4E6), and Hyb1H11 produced antibodies specific for malondialdehyde-modified LDL (mAb-1H11) alone. The IgG fraction of the antibodies was purified by affinity chromatography on protein A-Sepharose and the affinity of the purified IgGs was determined in a solid phase radioimmunoassay and/or in ELISA. The $K^a$ values of the monoclonal antibody mAb-4E6 were $<10^6$ $M^{-1}$ for native LDL and $>10^9$ $M^{-1}$ for malondialdehyde-modified LDL and copper-oxidized LDL. The $K_a$ values for the monoclonal antibody mAb-1H11 were $<10^6$ $M^{-1}$ for both LDL and OxLDL and $>10^9$ $M^{-1}$ for malondialdehyde-modified LDL. The $k_a$ values for the monoclonal antibody mAb-8A2, obtained after immunization of mice with LDL, were $>10^9$ $M^{-1}$ for all LDL forms. Delipidation of MDA-modified LDL and OxLDL resulted in a loss of the immunoreactivity of mAb-4E6, suggesting that it is directed against a conformational epitope in the protein moiety of oxidatively modified LDL.

Example 2

Use of mAb-4E6 for the Quantitation of OxLDL and MDA-Modified LDL in Coronary Lesions of Watanabe Heritable Hyerlipidemic Rabbits and Miniature Pigs on a Cholesterol Rich Diet Coronary arteries were obtained from 2 and 5 month old Watanabe heritable hyperlipidemic rabbits (n=30) on normal chow or from miniature pigs (n=26) which were fed a diet enriched in cholesterol (4%), saturated fat (14% beef tallow) and bile extract (1%) for 6 to 24 weeks.

Arterial specimens were submerged within 30 min after removal in PBS (pH 7.4) containing 4% sucrose, 20 µM vitamin E and 10 µM butylated hydroxytoluene as antioxidants, and 1 mM EDTA, snap-frozen in liquid nitrogen and stored at −80° C. Frozen 7 µM sections were stained with hematoxylin and eosin and with oil red 0 or immunostained as described below. Morphometric parameters of atherosclerotic lesions were measured by planimetry using the Leica 2 Quantimet color image analyzer (Cambridge, UK). The area within the external elastic lamina, the internal clastic lamina and the lumen were measured. Media was defined as the area between the internal and external clastic lamina. Intima was defined as the area within the internal elastic lamina not occupied by vessel lumen.

Oxidized apo B-100 containing lipoproteins were detected with the specific monoclonal antibody mAb-4E6, alkaline-phosphatase conjugated rabbit-anti-mouse IgG antibodies and the fuchsin alkaline phosphate substrate system (Dako, Carpinteria, Calif.), and the absorbance was measured in the color image analyzer. Specificity of immunostaining was confirmed by inhibition of staining with excess of copper-oxidized LDL but not with native LDL or with malondialdehyde-modified albumin. The staining colocalized with that monoclonal antibody mAb-13F6, specific for apo B-100. Absorbance (approximately 10%) measured with excess copper-oxidized LDL was presumed to represent background staining.

FIG. 1 illustrates the correlation between the levels of oxidized apo B-100 containing lipoproteins, i.e. OxLDL and MDA-modified LDL, in the lesions and the mean intimal area of coronary lesions in Watanabe hyperlipidemic rabbits (A) and in miniature pigs (B). Those data thus demonstrate a correlation between the accumulation of OxLDL and MDA-modified LDL and the progression of coronary atherosclerotic lesions in 2 different animal models. In Watanabe rabbits the progression of the lesions is due to the increase of LDL cholesterol associated with the heritable LDL receptor deficiency, whereas the progression in miniature pigs is due to a diet-induced increase in LDL cholesterol.

Example 3

Immunohistochemistry

1. Introduction

This example is a typical example of the use of the highly specific antibody mAb-4E6 in immunohisto-chemistry applied to human atherosclerotic lesions. In a similar manner corresponding experiments may be performed, for which certain conditions can be adapted by the skilled person using his common knowledge in the field.

2. Material and Methods

Coronary artery specimens, obtained at the time of transplantation from patients with ischemic heart disease (n=7) or dilated cardiomyopathy (n=7), were treated as described earlier (document 7). The specimens were collected within 30 min after removal of the heart in PBS (pH 7.4) containing 4% sucrose, 20 µM vitamin E and 10 µM butylated hydroxytoluene as antioxidants, and 1 mM EDTA, and were stored at −80° C. Frozen 7 µm thick sections were cut and stained with hematoxylin and eosin. Six to 8 sections at a distance of 84 µm were analyzed for each specimen to insure representative results. Duplicate slides were developed with monoclonal antibodies mAb-4E6, specific for oxidized LDL, PG-M1, specific for human macrophages, or 1A4, specific for human smooth muscle α-actin (both from Dako SA, Glostrup, Denmark). Specificity of binding of mAb-4E6 was confirmed by its inhibition with OxLDL but not with native LDL.

3. Results

Figure 2A:
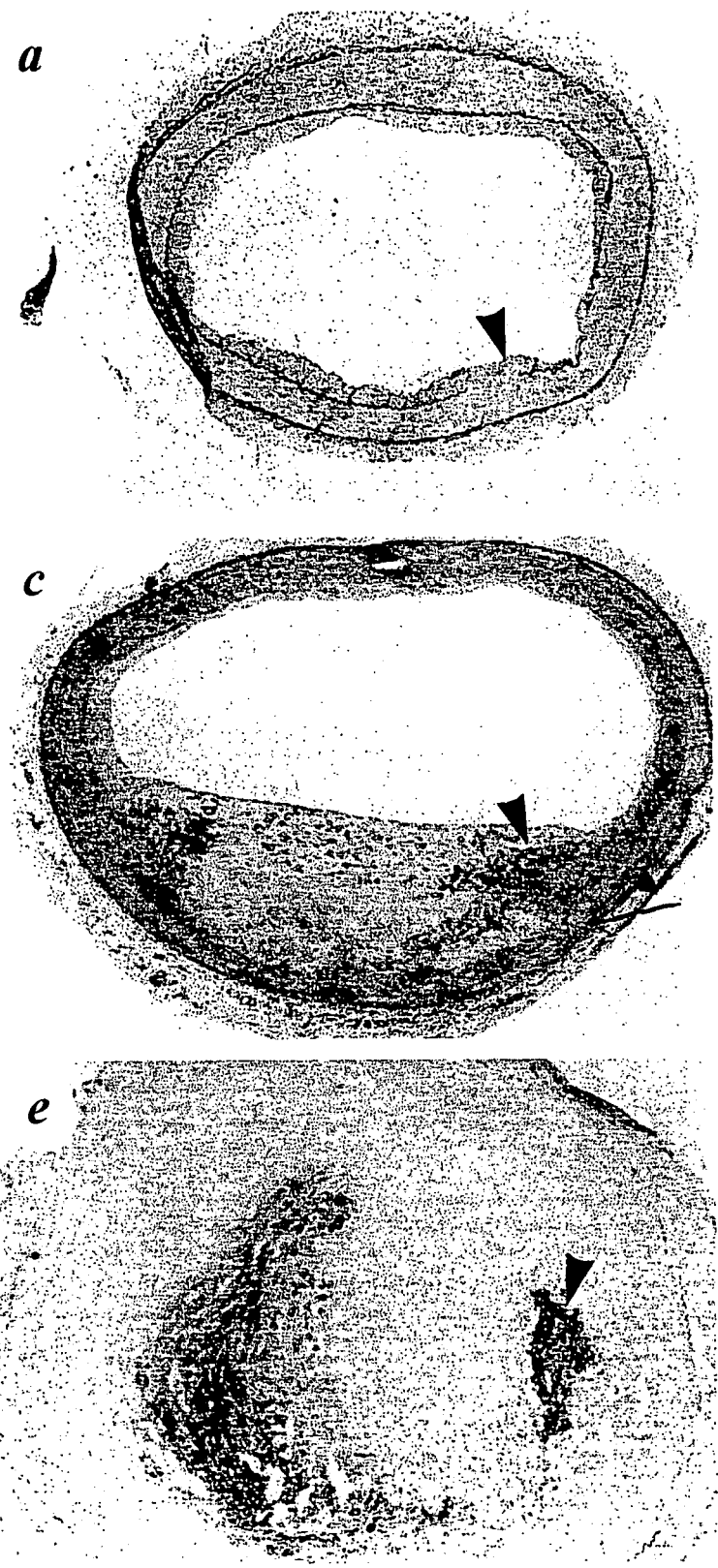
FIG. 2 illustrates the accumulation of OxLDL and MDA-modified LDL in coronary arteries of cardiac explants of ischemic heart disease but not of dilated cardiomyopathy patients.
Figure 2B:
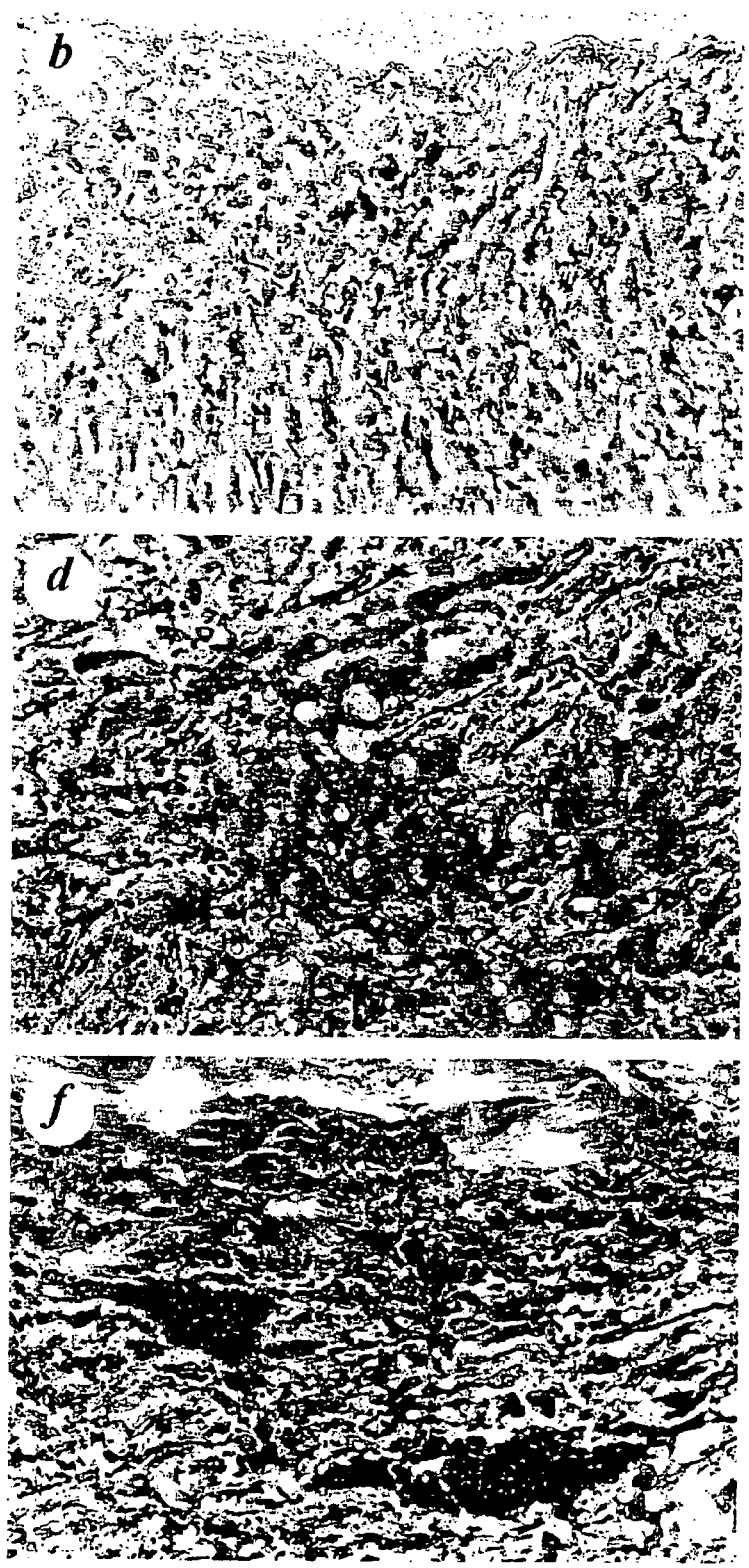

Coronary artery segments of 7 individuals with pretransplant dilated cardiomyopathy did not contain atherosclerotic lesions and the monoclonal antibody did not detect OxLDL and/or aldehyde-modified LDL in these segments. Coronary artery segments of 7 patients with pretransplant ischemic heart disease all contained atherosclerotic lesions which contained OxLDL and/or aldehyde-modified LDL (FIG. 2). This information is sufficient to state that the antibody detects OxLDL in atherosclerotic lesions in a highly specific manner.

OxLDL was associated with macrophage foam cells (preferentially in lesions with <50% stenosis), with smooth muscle foam cells and with the necrotic lipid core (preferentially in lesions with >50% stenosis). Macrophages and smooth muscle cells were identified by immunostaining with specific monoclonal antibodies (5). These data supported the hypothesis that oxidation of LDL may be associated with the development of ischemic coronary artery disease. The monoclonal antibody mAb-4E6 of the present invention that detected the immunoreactive material in the tissue sections was then further used in ELISA (cf. Example 4).

4. Legend to FIG. 2

Light micrographs (a, c, e; ×40) and phase contrast micrographs (b, d, f; ×400) of representative left anterior descending coronary artery specimens of a patient with dilated cardiomyopathy (male; 40 years of age) (a, b) and of a patient with ischemic heart disease (male; 57 years of age) (c-f). Tissue sections were immunostained with the monoclonal antibody mAb-4E6. Oxidized LDL was undetectable in the neointima of the first patient (a, b), but demonstrable in plaques of the second patient. The oxidized LDL was associated with macrophage foam cells that infiltrated at the shoulder areas of fibrous plaques (c, d) and with smooth muscle foam cells in fibrous caps (e, f).

Example 4

Competitive ELISA

1. Introduction

According to the invention an ELISA was established for the quantitation of OxLDL and aldehyde-modified LDL in plasma. It was based on the inhibition of the binding of mAb-4E6 to the wells of microtiter plates coated with copper-oxidized LDL. This antibody was obtained as described in Example 1.

2. Material and Methods

Standard OxLDL and aldehyde-modified LDL and plasma samples were diluted in PBS containing 1 mM EDTA, 20 µM vitamin E, 10 µM butylated hydroxytoluene, 20 µM dipyridamole and 15 mM theophylline to prevent in vitro LDL oxidation and platelet activation. Equal volumes of diluted purified mAb-4E6 solution (final concentration 7.5 ng/ml) and of diluted standard solution (copper-oxidized LDL added as competing ligand at a final concentration ranging from 50 to 500 ng/ml) were mixed and incubated for 30 min at room temperature. Then 200 µl aliquots of the mixtures were added to wells coated with MDA-modified LDL or OxLDL.

Samples were incubated for 2 h at room temperature. After washing, the wells were incubated for 1 h with horse-radish peroxidase conjugated rabbit IgG raised against mouse immunoglobulins and washed again. The peroxidase reaction was performed as described earlier (5) and the absorbance (A) was read at 492 nm.

Controls without competing ligand and blanks without antibody were included routinely. The percent inhibition of binding of mAb-4E6 to the immobilized ligand was calculated as:

$$\frac{A^{492\,nm}\text{control} - A^{492\,nm}\text{sample}}{A^{492\,nm}\text{control} - A^{492\,nm}\text{blank}}$$

and standard curves were obtained by plotting the percentage of inhibition vs the concentration of competing ligand.

The lower limit of detection was 0.020 mg/dl in undiluted human plasma. Intra- and interassay coefficients of variation were 10 and 12%, respectively. Standard OxLDL and aldehyde-modified LDL and plasma samples were diluted in PBS containing antioxidants and antiplatelet agents as described above.

3. Results

Figure 3:
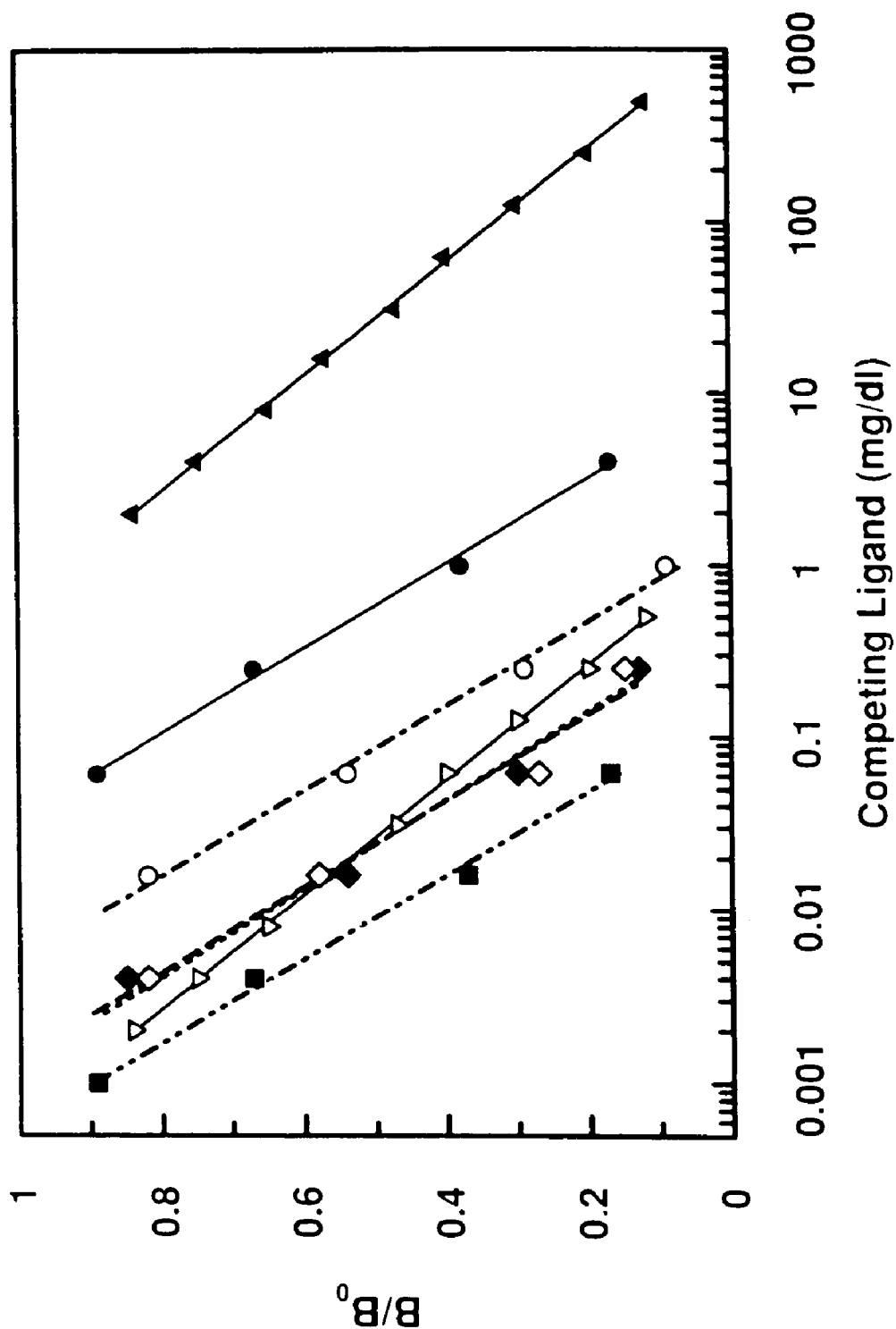
FIG. 3 illustrates the inhibition of the binding of mAb-4E6 to immobilized OxLDL by native LDL, OxLDL and MDA-modified LDL in solution.

The specificity of mAb-4E6 for OxLDL and aldehyde-modified LDL is illustrated in FIG. 3. 50% inhibition of binding of mAb-4E6 to immobilized OxLDL and aldehyde-modified LDL was obtained with 0.025 mg/dl copper-oxidized LDL and 25 mg/dl native LDL, respectively. The $C_{50}$ value, i.e., the concentration that is required to obtain 50% inhibition of antibody binding, increased from 2.5 mg/dl for MDA-modified LDL with 60 substituted lysine residues per apo B-100 molecule to 0.025 mg/dl for MDA-modified LDL with 240 substituted lysine residues per apo B-100 molecule (FIG. 3). Copper-oxidation resulted in fragmentation of the apo B-100 moiety but did not abolish the binding of mAb-4E6 (FIG. 3). 50-fold higher molar concentrations of MDA-modified albumin were required to obtain 50% inhibition (not shown), whereas up to 1,000-fold higher molar concentrations of MDA-modified lysine did not affect mAb-4E6 binding. OxLDL and aldehyde-modified LDL isolated from patient plasma had the same reactivity as MDA-modified LDL with 120 substituted lysines and as copper-oxidized LDL with 210 substituted lysines. Intra- and interassay coefficients of variation were 10 and 12%, respectively. When copper-oxidized LDL were added to human plasma at a final concentration of 0.25 and 2 mg/dl, respectively, recoveries were 95 and 105%, respectively.

4. Legend to FIG. 3

Interaction of mAb-4E6 with competing ligands in solution. Copper-oxidized LDL (1 μg/ml) was the plated antigen. mAb-4E6 was added in the absence and in the presence of competing ligands: copper-oxidized LDL (∇), MDA-modified LDL with 240 (□), 120 (◇), 90 (◯) and 60 (○) blocked or substituted or modified lysines per apo B-100, respectively, native LDL (Δ), and OxLDL and aldehyde-modified LDL (◇) isolated from the plasma of severe chronic renal failure patients. Results are expressed as $B/B_0$ where $B_0$ is the amount of mAb-4E6 bound in the absence and B that amount bound in the presence of competing ligand.

Example 5

Sandwich ELISA

1. Introduction

According to the invention a sandwich-type ELISA was established for the quantitation of OxLDL and aldehyde-modified LDL in plasma. It was based on the binding of immunoreactive material to the wells of microtiter plates coated with the monoclonal antibody mAb-4E6 and the detection of bound immunoreactive material with the use of the monoclonal antibody mAb-8A2 labeled with peroxidase. This version of the ELISA is more suited for use in the clinical laboratory because it overcomes the need to prepare standard solutions of in vitro oxidized and/or aldehyde-modified LDL which can only be kept at −4° C. for a limited period of time, typically 2 weeks. MDA-modified LDL may be added to reference plasma and those standard preparations may be stored at −80° C. for up to 1 year (see above).

2. Material and Methods

Standard preparations and plasma samples were diluted in PBS containing antioxidants and antiplatelet agents as described above, 180 μl aliquots of 80-fold diluted plasma and of standard solutions containing between 10 and 0.01 nM of malondialdehyde-modified LDL were applied to the wells of microtiter plates coated with mAb-4E6 (200 μl of a 4 μg/ml IgG solution) and incubated for 2 h at room temperature. After washing, the wells were incubated for 1 h with horseradish peroxidase conjugated mAb-8A2, IgG (final IgG concentration 65 ng/ml) and washed again. The peroxidase reaction was performed as described above. The absorbance measured at 492 nm correlates with the log-value of the aldehyde-modified LDL concentration in the range between 1.5 nM and 0.3 nM.

Figure 4:
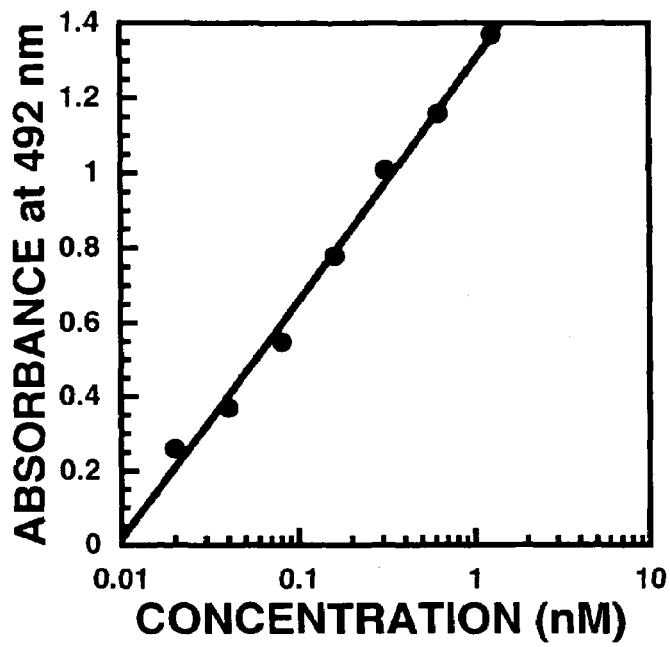
FIG. 4 illustrates a typical standard curve obtained with MDA-modified LDL in sandwich ELISA.

3. Legend to FIG. 4

Standard curves for the sandwich ELISA mAb-4E6 was the plated antibody. MDA-modified LDL was the ligand. Bound MDA-modified LDL was detected with mAb-8A2 conjugated to horse radish peroxidase. MDA-modified LDL was added to 8 different plasma samples to a final concentration of 100 nM and further diluted in buffer to final concentrations ranging from 2 to 0.2 nM.

Example 6

Use of the ELISA in Diagnosis of Posttransplant Coronary Artery Disease

1. Introduction

The ELISA of the present invention was used to study the association between plasma levels of OxLDL and aldehyde-modified LDL and posttransplant coronary artery disease.

2. Material and Methods 2.1. Patients

The posttransplant study group contained 47 patients transplanted for dilated cardiomyopathy and 60 patients treated for ischemic heart disease. The clinical characteristics of these patients are summarized in Table 1. At the time of blood sampling, between 12 and 84 months after surgery, all patients were in a stable cardiac condition without evidence of acute rejection. From 14 patients (7 dilated cardiomyopathy and 7 ischemic heart disease patients) coronary arteries of cardiac explants were isolated and studied by immunohisto-chemistry (as demonstrated in Example 3).

Adequate information about smoking habits was available for 92 of the 107 patients (16 smokers and 76 non-smokers). There was no adequate information about smoking habits of donors. Blood samples of 53 non-smoking controls (25 males/28 females; age: 52±1.3 years) without a history of atherosclerotic cardiovascular disease were obtained. The controls were matched for age, gender and levels of LDL cholesterol. They were selected from the laboratory and clinical staff.

2.2. Coronary Angiography

Routine annual coronary angiograms were available for all posttransplant patients at the time of blood sampling. Coronary artery disease was independently assessed by two angiographers who where unaware of the OxLDL and aldehyde-modified LDL levels and was visually graded as follows:

grade 0: normal coronary arteries grade I: minor abnormalities with <50% stenosis of primary or secondary branches and normal left ventricular function grade II: $\geq$50% stenosis of primary or secondary branches, or distal involvement with impaired left ventricular function.

It is well known that angiography systematically underestimates the extent of coronary intimal thickening in cardiac transplant recipients. This study therefore does not attempt to accurately quantify the coronary artery disease in our patients. Rather the subdivision in groups defined above relies on angiographic data that are easily distinguishable and that have been shown to correlate with histopathologic findings. Out of 107 patients, 46 patients had a normal coronary angiogram 3 years before and development of angiographic, coronary artery disease within a 3 year follow-up period was assessed in all these patients. The reference normal coronary angiogram was the first post-operative angiogram in 18 patients, the second in 14 patients and the third in 14 patients.

The study was approved by the Institutional Review Board and the study subjects provided informed consent.

2.3. Blood Sampling

Venous blood samples from patients and controls were collected on 0.1 vol of 0.1 M citrate, containing 1 mM EDTA, 20 μM vitamin E, 10 μM butylated hydroxytoluene, 20 μM dipyridamole and 15 mM theophylline to prevent in vitro LDL oxidation and platelet activation. Blood samples were centrifuged at 3,000 g for 15 min at room temperature within 1 h of collection and stored at −20° C. until the assays were performed.

2.4. Lipoproteins: Isolation and Modification

LDL were isolated from pooled sera of fasting normolipidemic donors by density gradient ultra-centrifugation (document 6). Standard preparations of MDA-modified and copper-oxidized LDL were prepared as described elsewhere (7, 8) and were used as assay controls. Apo B-100 molecules of in vitro MDA-modified LDL (7) and of copper-oxidized LDL (8) contained on average 244, and 210 substituted lysines (out of a total of 356), respectively (5, 9). Whereas the extent of lysine-substitution in in vitro MDA-modified LDL and copper-oxidized LDL is very similar, the lipid moiety of the former is not oxidized. Specificity of the monoclonal antibody mAb-4E6 for both MDA-modified LDL and copper-oxidized LDL suggests that it depends on the extent of protein (lysine) modification only. All lipoprotein concentrations were therefore expressed in terms of protein. OxLDL and aldehyde-modified LDL isolated from the plasma of patients were:characterized as described previously (5, 9).

2.5. Assays

Cholesterol and triglycerides were measured by enzymatic methods (Boehringer Mannheim, Meylon, France). Typing of major histocompatibility complex class I (HLA-B) and class II (HLA-DR) antigen was performed by the microlymphocytotoxicity technique.

The ELISA of the invention was used to detect OxLDL and aldehyde-modified LDL.

2.6. Statistical Analysis

Controls and patients were compared by ANOVA test followed by nonparameteric Mann-Whitney or Dunnett's multiple comparison test on logarithmically transformed values, in the Instat V2.05a statistical program (Graph Pad Software, San Diego, Calif.). Non-quantitative parameters were compared by Chi-square analysis. OxLDL and aldehyde-modified LDL levels measured in 3 aliquots of the same plasma samples were compared in Friedman nonparametric repeated measures test. Logistic regression analysis, using the SAS software (SAS Institute Inc., USA), was performed to evaluate the correlation between angiographically assessed coronary artery stenosis (as dependent variable) and plasma levels of OxLDL and aldehyde-modified LDL, age and sex of recipients, age and sex of donors, pretransplant history of ischemic heart disease or dilated cardiomyopathy, duration of ischemia, length of follow up, number of rejections, number of HLA-mismatches, cytomegalovirus infection, hypertension (antihypertensive treatment), diabetes, treatment with lipid lowering drugs (statins or fibrates) and serum levels of LDL cholesterol, HDL cholesterol and triglycerides as independent variables. p-values of less than 0.05 were considered to indicate statistical significance. Logistic regression analysis was also performed to evaluate the correlation between plasma levels of OxLDL and aldehyde-modified LDL and development of coronary artery stenosis during a 3-year follow-up period.

3. Results

The correlation between OxLDL and aldehyde-modified LDL and coronary artery stenosis was evaluated in 47 patients transplanted for dilated cardiomyopathy and in 60 patients treated for ischemic heart disease. Analysis of clinical data for the two groups of heart transplant patients (Table 1) revealed no significant differences in age and gender of the recipients, age and gender of donors, duration of ischemia of the donor heart, number of rejection episodes, number of HLA-mismatches, frequency of Cytomegalovirus infections, hypertension or diabetes, and grade of coronary artery stenosis. Patients transplanted for ischemic heart disease were followed longer and received more frequently lipid lowering drugs (Table 1).

Analysis of the laboratory data (Table 2) revealed no significant differences in serum levels of triglycerides, HDL cholesterol and LDL cholesterol between groups of patients or between patients and controls. However, significant differences in levels of OxLDL and aldehyde-modified LDL were observed. Mean plasma levels of OxLDL and aldehyde-modified LDL were 1.3±0.14 mg/dl in dilated cardiomyopathy patients (p<0.001 vs controls) and 1.7±0.13 mg/dl in ischemic heart disease patients (p<0.001 vs controls and <0.01 vs dilated cardiomyopathy patients) (Table 2). Plasma levels of OxLDL and aldehyde-modified LDL in control subjects matched for age, gender and serum levels of triglycerides, HDL cholesterol and LDL cholesterol were 0.60±0.034 mg/dl (n=53; p<0.001 vs both transplanted dilated cardiomyopathy and ischemic heart disease patients).

Levels of OxLDL and aldehyde-modified LDL were not different in samples that were stored for 24 h to 4 months after collection, and up to four thawing and freezing cycles did not cause an increase of OxLDL and aldehyde-modified LDL levels. These findings indicated that the addition of EDTA, antioxidants and anti-platelet agents adequately prevented the in vitro oxidation of LDL. In a subset of 87 consecutive plasma samples levels of OxLDL and/or aldehyde-modified LDL were measured in 3 separate aliquots on 3 different days. The levels were 1.30±0.074 mg/dl, 1.48±0.101 mg/dl and 1.46±0.090 mg/dl, respectively. Friedman nonparametric repeated measures test revealed no significant differences.

Figure 5:
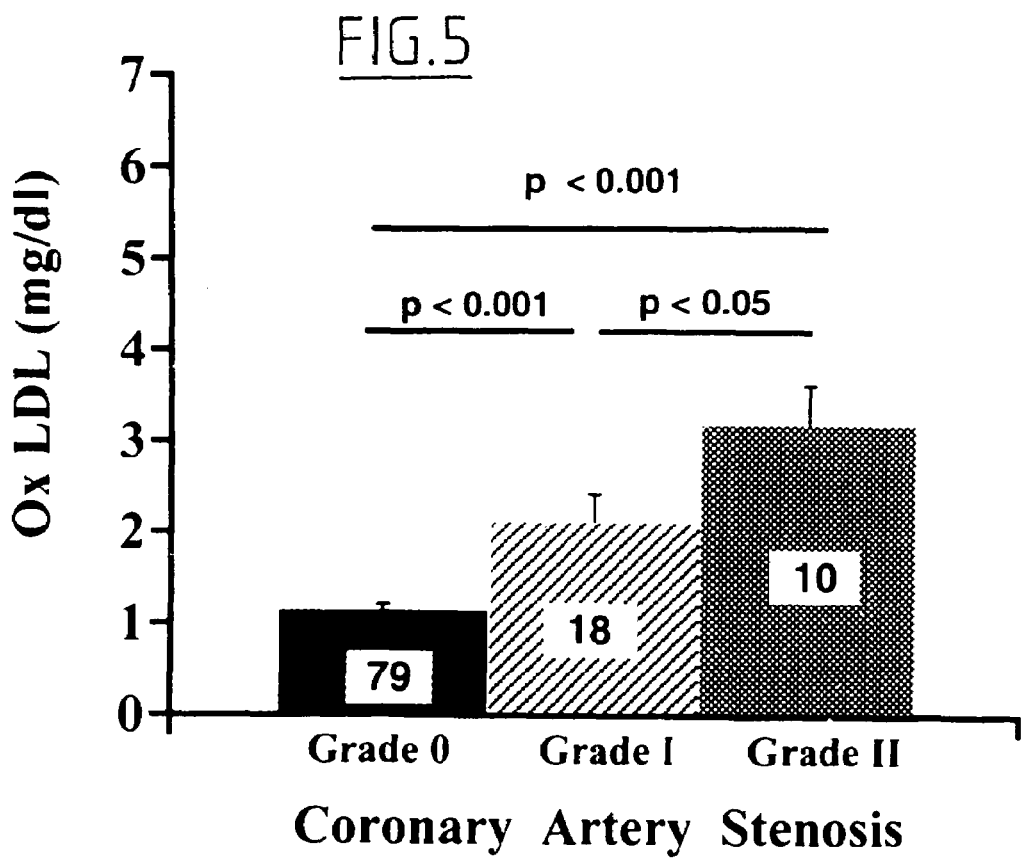
FIG. 5 illustrates levels of OxLDL and aldehyde-modified LDL in posttransplant plasma samples of heart transplant patients with different extents of angiographically assessed coronary artery stenosis.

Mean OxLDL and aldehyde-modified LDL levels were 1.2±0.053 mg/dl (n=79) in posttransplant samples of patients with angiographically normal coronary arteries (grade 0), 2.1±0.30 mg/dl in patients with grade I coronary artery stenosis (n=18; p<0.001 vs grade 0) and 3.2±0.45 mg/dl in patients with grade II coronary artery stenosis (n=10; p<0.001 vs grade 0 and p<0.05 vs grade I) (FIG. 5). Serum levels of LDL cholesterol, triglycerides and HDL cholesterol were very similar in patients with higher grade of coronary artery stenosis. Levels of OxLDL and aldehyde-modified LDL in plasma samples of patients transplanted for dilated cardiomyopathy or ischemic heart disease, with the same grade of coronary artery stenosis, were similar: 1.1±0.072 and 1.4±0.079 mg/dl for grade 0 patients and 2.6±0.60 and 2.4±0.29 mg/dl for patients with higher grade of coronary artery stenosis. The number of patients with elevated levels of OxLDL and aldehyde-modified LDL (>1 mg/dl, i.e. mean levels of controls+2 SD) were 43 (out of 60) in the subpopulation of patients with pretransplant ischemic heart disease and 21 (out of 47) in the subpopulation of patients with pretransplant dilated cardiomyopathy. Forty-two out of 79 patients with angiographically normal coronary arteries had elevated levels of OxLDL and aldehyde-modified LDL. Elevated levels were detected in 12 (out of 18) patients with grade I and in all patients with grade II stenosis (p=0.0046 for trend).

To allow further characterization of the immunoreactive material detected in the ELISA, LDL fractions were isolated from the plasma of all of 10 patients with grade II coronary artery stenosis (18). These fractions retained 85±10% (mean±SD) of the immunoreactive material, whereas no immunoreactive material migrated in the serum albumin position. OxLDL and aldehyde-modified LDL were isolated from isolated LDL fractions by ion-exchange chromatography on a mono Q-Sepharose column with a recovery of 75%. The number of substituted lysines per apo B-100 molecule was 130±10 for OxLDL and aldehyde-modified LDL compared to 5±1 (p<0.001) for native LDL. The respective cholesterol/protein ratios were 3.3±0.54 and 1.8±0.36 (p<0.001). The levels of arachidonate and linoleate in OxLDL and aldehyde-modified LDL isolated from the plasma of these patients were 75 and 80% lower than these in native LDL isolated from the same plasma samples. The inhibition curves obtained with OxLDL and aldehyde-modified LDL isolated from the plasma of heart transplant patients were superimposable with these obtained with in vitro oxidized LDL with the same extent of protein modification (120 substituted lysines per apo B-100 molecule) (FIG. 3).

The protein/antigen ratio and the relative reactivity in the ELISA of OxLDL and aldehyde-modified LDL isolated from the plasma of these patients were similar to these of copper-oxidized or MDA-modified standard LDL preparations.

Logistic regression analysis (Table 3) identified 3 parameters that were significantly and independently correlated with posttransplant coronary artery stenosis including levels of OxLDL and aldehyde-modified LDL, length of follow up and donor age.

In contrast, pretransplant history of dilated cardiomyopathy or of ischemic heart disease, age and gender of recipients, gender of donors, duration of ischemia of the donor heart, extent of HLA-mismatch, number of rejections, hypertension, diabetes, and serum levels of LDL cholesterol, HDL cholesterol and triglycerides in recipients did not significantly contribute to the individual variations in extent of coronary artery stenosis (Table 3).

Serum levels of LDL cholesterol, HDL cholesterol and triglycerides in patients were similar to these in controls (Table 2), so that higher grade of coronary artery stenosis was unlikely to depend on these variables in this study group. Fifty-six of the 107 transplant patients received lipid lowering drugs (46 with statins and 10 with fibrates) (Table 1), but the treatment with these drugs was not correlated with the incidence of angiographic graft vasculopathy (Table 3). Seventy-five (out of 107) patients were treated with calcium channel blockers. The plasma levels of OxLDL and aldehyde-modified LDL in these patients (1.53±0.11 mg/dl) were very similar to these in non-treated patients (1.74±mg/dl) and treatment with these drugs was not correlated with the extent of coronary artery stenosis.

Development of coronary artery disease was observed in 12 out of 46 heart transplantation patients during a 3-year follow-up period. There were no differences in age and gender of recipients, age and gender of donors, duration of ischemia, extent of HLA mismatch, frequency of cytomegalovirus infections, hypertension and diabetes (Table 4) nor in serum levels of triglycerides, HDL cholesterol and LDL cholesterol (Table 5) between patients without and with development of coronary artery disease. However, levels of OxLDL and aldehyde-modified LDL were significantly elevated in patients with development of coronary artery disease (Table 5).

Logistic regression analysis revealed that plasma levels of OxLDL and aldehyde-modified LDL (Chi-square value=7.1; p=0.0076) and age of donor (Chi-square value=4.4; p=0.035) predicted the development of coronary artery disease in these patients. Three of these patients developed coronary artery disease in the first year, 3 in the second and 6 in the third year. The plasma levels of OxLDL and aldehyde-modified LDL were 3.9±0.6 mg/dl, 2.0±0.37 mg/dl and 1.2±0.33 mg/dl, respectively. Although statistical analysis showed no correlation with gender, hypertension and Cytomegalovirus infection, 8 out of 12 of these patients were male, hypertensive and had Cytomegalovirus infection.

4. Discussion

This demonstrates:

1) that cardiac explants of patients with ischemic heart disease, but not with dilated cardiomyopathy, contain oxidized LDL in macrophages and in smooth muscle cells in atheromatous plaques;

2) that posttransplant coronary artery disease is associated with increased plasma levels of OxLDL and aldehyde-modified LDL both in patients transplanted for dilated cardiomyopathy or for ischemic heart disease, and 3) that increased plasma levels of OxLDL and aldehyde-modified LDL correlate with the development of coronary artery stenosis.

OxLDL and aldehyde-modified LDL levels in plasma samples of heart transplant patients without angiographically detectable coronary artery lesions were 2-fold higher than in plasma samples of control subjects without a history of atherosclerotic cardiovascular disease, who were matched for age, gender, and plasma levels of LDL cholesterol, HDL cholesterol and triglycerides. A further 2.7-fold increase was observed in posttransplant plasma samples of patients with pronounced coronary artery stenosis. These data suggest that elevated plasma levels of OxLDL and aldehyde-modified LDL may be an indicator of posttransplant coronary artery stenosis. Increased plasma levels of OxLDL and aldehyde-modified LDL correlated with the extent of coronary artery stenosis and also with its progression, suggesting that OxLDL and aldehyde-modified LDL may play a pathogenic role in the accelerated progression of coronary artery disease in heart transplant patients.

It has been suggested that posttransplant atherosclerosis results from a "response to injury" of the endothelium (10). The extent of ischemic injury in endomyocardial biopsies was indeed found to be a strong predictor of the development of accelerated atherosclerosis (11–13). Endothelial injury may be induced by cellular delayed-type hypersensitivity immune responses elicited by class II histocompatibility (HLA) antigens on coronary artery endothelium (14), by cytomegalovirus infection (15, 16), by cyclosporin (17) and by OxLDL and aldehyde-modified LDL (18) that may act synergistically with cyclosporin (19). In the present study, the extent of histoincompatibility between pairs of donors and recipients, the number of episodes of rejection or Cytomegalovirus infection did not correlate with the grade of coronary artery stenosis, whereas OxLDL and aldehyde-modified LDL were significantly and independently correlated with posttransplant coronary artery disease. The observed association between the age of the donor and the occurrence of coronary artery disease is in agreement with previous findings that coronary atherosclerosis in the donor heart predisposes to accelerated posttransplant coronary artery stenosis (20).

OxLDL and aldehyde-modified LDL were demonstrated in coronary arteries in cardiac explants of ischemic heart disease patients suggesting that OxLDL and aldehyde-modified LDL that accumulate in the arterial wall may contribute to the progression of coronary artery stenosis. The cholesterol/protein ratio in OxLDL and aldehyde-modified LDL was very similar to that in LDL extracted from atherosclerotic lesions as described previously (21,22). A possible explanation is that at least part of the OxLDL and aldehyde-modified LDL is released from the arterial wall. Previously, we have demonstrated that plaque rupture in acute myocardial infarction patients is associated with the release of oxidatively modified LDL (5).

In vitro data suggest that OxLDL and aldehyde-modified LDL may be linked to atherogenesis by a sequence of events (reviewed in 2,23). Endothelial cells exposed to OxLDL and aldehyde-modified LDL secrete adhesion molecules, chemoattractant proteins and colony-stimulating factors that enhance the infiltration, proliferation and accumulation of monocytes/macrophages in the arterial wall. Uptake of OxLDL and aldehyde-modified LDL by infiltrated macrophages may result in the generation of foam cells that produce oxygen radicals and thus further contribute to the oxidation of LDL. It has been demonstrated that OxLDL and aldehyde-modified LDL inhibit the migration of aortic endothelial cells in vitro, suggesting that OxLDL and aldehyde-modified LDL may limit the healing response of the endothelium after injury, and that basic fibroblast growth factor reverses the atherosclerosis associated impairment of human coronary angiogenesis-like responses in vitro (24, 25). OxLDL and aldehyde-modified LDL may also contribute to rapidly progressing coronary atherosclerosis by inducing platelet adhesion, by decreasing the anticoagulant and fibrinolytic capacities of activated endothelium and by impairing vasodilation and inducing shear stress (2,23).

Increased intracellular levels of ferritin (26) or of alpha-tocopherol analogs (27) decreased the extent of endothelial injury elicited by OxLDL and aldehyde-modified LDL in vitro, whereas antioxidants protect against progression of atherosclerosis in experimental animals (reviewed in document 28).

In summary, the present example demonstrates that posttransplant atherosclerosis correlates with plasma levels of OxLDL and aldehyde-modified LDL.

5. Legend to the FIG. 5

Plasma levels of OxLDL and aldehyde-modified LDL and angiographically assessed grade of coronary artery stenosis. Grade 0: normal coronary arteries; grade I: minor abnormalities with <50% stenosis of primary or secondary branches and normal left ventricular function; and grade II: ≧50% stenosis of primary or secondary branches, or distal occlusions with impaired left ventricular function.

EXAMPLE 7

Use of the ELISA in Renal Failure Patients

1. Material and Methods 1.1. Subjects

The patient population consisted of 20 mild chronic renal failure (MCRF) and 77 severe chronic renal failure patients:

21 on conservative treatment including dietary and antihypertensive treatment (SCRF), and 56 on a four-hour, three times a week hemodialysis schedule (HEMO) for 66 months (95% CI, 50–82 months). All hemodialysis patients were given an oral polyvitamin preparation (Ol-Amine, La Meuse, Belgium) after hemodialysis, which contained only minute amounts of antioxidant compounds (i.e. 5 mg of vitamin E and 100 mg of vitamin C). Controls and non-dialyzed patients did not receive routine prescriptions of vitamin supplements. The high frequency of atherosclerotic disease in these patients (Table 6) is in agreement with previously published data (29, 30). The diagnosis of atherosclerotic heart disease, cerebrovascular disease and peripheral vascular disease was made after reviewing the patient files for a history of myocardial infarction, unstable angina or antianginal treatment, cerebrovascular accidents, transient ischemic attack or events related to peripheral vascular disease such as ischemic ulcera, amputation or bypass surgery. Angiograms were available for only a few patients. No patients had evidence of unstable atherosclerotic disease at the time of blood sampling nor in the following days. A group of 27 healthy volunteers (Table 6) without a history of renal disease or atherosclerotic vascular disease served as controls. Patients receiving lipid lowering drugs were excluded. The study was approved by the Institutional Review Board and the study subjects provided informed consent.

1.2. Blood Samples

Venous blood samples from patients and controls were collected on 0.1 vol of 0.1 M citrate, containing 1 mM EDTA, 20 μM vitamin E, 10 μM butylated hydroxytoluene, 20 μM dipyridamole and 15 mM theophylline to prevent in vitro LDL oxidation and in vitro platelet activation, respectively. Blood samples were centrifuged at 3,000 g for 15 min at room temperature within 1 h of collection and stored at −20° C. until the assays were performed.

1.3. Assays

Titers of autoantibodies against OxLDL and aldehyde-modified LDL and native LDL were measured according to Salonen et al. (3) as described in detail elsewhere (5). vWF antigen levels were measured in a sandwich-type ELISA based on a polyclonal rabbit anti-human vWF antiserum (Dako, Glostrup, Denmark), horseradish peroxidase-conjugated rabbit anti-human vWF IgG (Dako) and o-phenylenediamine. Plasma levels of total cholesterol, HDL cholesterol and triglycerides were determined using standard enzymatic assays (Boehringer Mannheim, Meylon, France). The LDL cholesterol levels were calculated using the Friedewald formula. For the patients not in hemodialysis, creatinine clearance rates were calculated from plasma creatinine levels using the Cockcroft and Gault formula (31).

1.4. Statistical Analysis

Controls and patients were compared by ANOVA test followed by Dunnett's multiple comparison test, in the Instat V2.05a statistical program (Graph Pad Software, San Diego, Calif.). Correlation coefficients were calculated according to Spearman. Multiple regression analysis, using the SAS software (SAS Institute Inc., USA), was performed to study the relationship between OxLDL and aldehyde-modified LDL as dependent variable, and age, sex, hypertension (antihypertensive treatment), levels of triglycerides, HDL cholesterol, LDL cholesterol and creatinine clearance rates (marker of extent of renal failure) and levels of vWF (marker of endothelial injury) as independent variables.

2. Results

Mean plasma levels of OxLDL and aldehyde-modified LDL in controls were 0.59 mg/dl (95% CI, 0.52–0.66 mg/dl; n=27), and were 2.7-fold higher in MCRF patients (p<0.01 as determined by Dunnett's multiple comparison test), 3.1-fold higher in SCRF patients (p<0.001), and 5.4-fold higher in HEMO patients (p<0.001) (Table 7). OxLDL and aldehyde-modified LDL levels were inversely correlated with creatinine clearance rates (r=−0.65; p<0.001; n=73). HEMO patients were not included in this analysis because their plasma creatinine clearance cannot be determined adequately.

In a series of 14 hemodialyzed patients, levels of OxLDL and in LDL were found to be very similar in fresh and in fresh frozen plasma samples. Three freezing and thawing cycles did not cause an increase of OxLDL and aldehyde-modified LDL, indicating that addition of antioxidants and antiplatelet agents prevented in vitro oxidation.

Plasma samples were obtained from 14 hemodialyzed patients on 3 consecutive days before the start of the dialysis procedure. The levels of OxLDL and aldehyde-modified LDL in these samples were similar: 3.4±0.25 mg/dl, 3.2±0.21 mg/dl and 3.5±0.28 mg/dl, respectively. Furthermore, plasma samples were obtained during (after 2 h) and at the end (after 4 h) of hemodialysis. Plasma levels of OxLDL and aldehyde-modified LDL were 4.0±0.60 mg/dl and 4.7±0.70 mg/dl (p=NS vs before) as compared to 3.4±0.25 mg/dl before the start of the dialysis procedure. Thus the hemodialysis procedure did not induce a significant increase in the OxLDL and aldehyde-modified LDL levels.

Adequate information about smoking habits was only available for controls (27 non-smokers) and for HEMO patients (12 smokers and 45 non-smokers). Levels of OxLDL and aldehyde-modified LDL were somewhat higher in smoking HEMO patients (3.6 mg/dl; 95% CI, 2.1–5.6 mg/dl) than in non-smoking HEMO patients (3.0 mg/dl; 95% CI, 2.5–3.6 mg/dl; p=NS). The plasma levels of OxLDL and aldehyde-modified LDL in hemodialyzed patients with a history of unstable atherosclerotic cardiovascular disease were 3.5±0.40 mg/dl (n=30) as compared to 2.8±0.60 mg/dl (n=26, p=NS) in hemodialyzed patients without a history of unstable atherosclerotic cardiovascular disease.

LDL fractions were isolated from the plasma of controls, of 10 MCRF patients, of 10 SCRF patients and of 10 HEMO patients by gel filtration on a Superose 6HR 10/30 column, as described previously (5). 75±6% (mean±SD), 80±4%, 83±6% and 79±5% of the immunoreactive material was recovered in the LDL fractions. No immunoreactive material migrated in the serum albumin position. The inhibition curves obtained with the respective LDL fractions were parallel to those obtained with in vitro copper-oxidized or MDA-modified standard LDL preparations. OxLDL and aldehyde-modified LDL were isolated from isolated LDL fractions of 10 SCRF patients by ion-exchange chromatography on a mono Q-Sepharose column with a recovery of 75%. Their physicochemical properties are summarized in Table 8. The levels of arachidonate of OxLDL and aldehyde-modified LDL isolated from these patients were reduced with 75%, whereas its linoleate levels were reduced with 80%. Thirty-seven % of the lysine residues of OxLDL were substituted with aldehydes. The inhibition curves obtained with OxLDL and aldehyde-modified LDL isolated from the plasma of chronic renal failure patients were parallel to these obtained with OxLDL and aldehyde-modified LDL that was obtained by in vitro oxidation of LDL that had been isolated from the plasma of control subjects (FIG. 3). The protein/antigen ratio and the relative reactivity in the ELISA of OxLDL and aldehyde-modified LDL isolated from the plasma of these patients were similar to these of copper-oxidized or MDA-modified standard LDL preparations (Table 8).

Titers of autoantibodies against OxLDL and aldehyde-modified LDL were 4.2 (95% CI, 4.0–4.4) in controls, were similar in MCRF and SCRF patients, but significantly increased in HEMO patients (p<0.001) (Table 7). Autoantibody titers correlated with levels of OxLDL and aldehyde-modified LDL in SCRF patients (r=0.44; p=0.047) and in HEMO patients (r=0.37; p=0.0055) (FIG. 6). No circulating autoantibodies against native LDL could be detected.

Levels of vWF were 100 percent in controls (95% CI, 90–110 percent), and were 1.5-fold higher in MCRF patients (p=NS vs controls), 1.6-fold higher in SCRF patients (p<0.01) and 2.1-fold higher (p<0.001) in HEMO patients (Table 7). Levels of vWF were not significantly higher in smoking HEMO patients (250 percent; 95%, 150–340 percent; n=12) than in non-smoking HEMO patients (220 percent; 95% CI, 190–260 percent; n=45). Levels of vWF correlated with levels of OxLDL and aldehyde-modified LDL in MCRF patients (r=0.59; p<0.0057), in SCRF patients (r=0.69; p=0.0006) and in HEMO patients (r=0.62; p<0.0001) (FIG. 7). In contrast, levels of vWF did not correlate with LDL cholesterol levels or with body weight.

Multiple regression analysis revealed that the extent of renal failure (F=14; p=0.0004) and the extent of endothelial injury (F=26; p=0.0001), but not age, sex, hypertension, triglyceride levels, HDL cholesterol or LDL cholesterol levels, accounted for a significant fraction of the variations in OxLDL and aldehyde-modified LDL levels (Table 9). Even when only subjects without evidence of ischemic atherosclerotic disease (n=53) were included in the model ($R^2$-value=0.68) only the extent of renal failure (F=21; p=0.0001) and the extent of endothelial injury (F=14; p=0.0006) contributed significantly to the variations in OxLDL and aldehyde-modified LDL levels. No other variables contributed significantly to these variations after exclusion of subjects without evidence of ischemic atherosclerotic disease. When only subjects with evidence of ischemic atherosclerotic disease (n=15) were included only the extent of endothelial injury (F=6.2; p=0.047; $R^2$-value=0.65) contributed to the variations in OxLDL and aldehyde-modified LDL levels. Exclusion of diabetic patients did not significantly change the data either. After exclusion of the extent of renal failure as an independent variable, multiple regression analysis revealed that hemodialysis (F=5.6; p=0.021; n=77), LDL cholesterol levels (F=7.1; p=0.0095) and endothelial injury (F=35; p=0.0001) accounted for a significant fraction of the variation in OxLDL and aldehyde-modified LDL levels in severe chronic renal failure patients (Table 10).

3. Discussion

In vitro work and experimental animal data suggest that oxidized LDL (OxLDL and aldehyde-modified LDL) may contribute to the progression of atherosclerosis (reviewed in document 2), and OxLDL and aldehyde-modified LDL have been demonstrated in human atherosclerotic plaques (5). The immuno-assay of this invention identifies OxLDL and aldehyde-modified LDL (MDA-modified LDL) with ≧60 substituted lysines per apo B-100 molecule, which represents the threshold of substitution required for scavenger receptor mediated uptake (1). Increased levels of OxLDL and aldehyde-modified LDL have been measured by ELISA in the plasma of chronic renal failure patients.

Overall, 80 percent of the immunoreactive material isolated from the plasma of patients was recovered in the LDL fractions that were separated by gel filtration. No immunoreactive material migrated in the albumin position. Inhibition curves obtained with the isolated OxLDL and aldehyde-modified LDL were parallel to these of in vitro copper-oxidized or MDA-modified LDL standard preparations and the protein/antigen ratio and the $C_{50}$ value of the isolated OxLDL and aldehyde-modified LDL were identical to these of standard OxLDL and aldehyde-modified LDL preparations. These data suggested that increased immunoreactivity of OxLDL and aldehyde-modified LDL fractions in plasma of these patients with the antibodies of this invention depended indeed on the higher extent of protein modification and not on changes in lipid composition as was previously observed with other antibodies (32). The increased electrophoretic mobility, the increased lysine modification, the increased cholesterol/protein ratio, the decreased arachidonic acid and linoleate levels were very similar to these of modified LDL extracted from atherosclerotic lesions (21, 22). OxLDL and aldehyde-modified LDL induced foam cell generation, suggesting that OxLDL and aldehyde-modified LDL were not "minimally modified" LDL.

Multiple regression analysis revealed that chronic renal failure and endothelial injury contributed significantly to the variation in OxLDL and aldehyde-modified LDL levels even when patients with evidence of ischemic atherosclerotic disease were excluded. Indeed, 79.6% and 82.4% of the variations in OxLDL and aldehyde-modified LDL levels could be explained in these models. No patients had evidence of unstable atherosclerotic disease at the time of blood sampling nor in the following days and exclusion of patients with a history of ischemic atherosclerotic disease did not affect the contribution of the extent of renal failure and of endothelial injury to the variations in OxLDL and aldehyde-modified LDL.

LDL cholesterol levels in controls and patients were very similar and LDL cholesterol levels did not contribute to the variations in OxLDL and aldehyde-modified LDL levels. Sutherland et al. (33) demonstrated that the lag time of conjugated diene formation, which is a measure for the sensitivity of LDL to in vitro oxidation, was similar in patients with chronic renal failure and in matched controls.

The maximum rate and the extent of LDL oxidation were even lower in patients with renal disease than in controls, due to lower levels of linoleic acid and higher levels of oleic acid. Furthermore, Schulz et al. (34) demonstrated that despite the fact that hemodialysis causes leukocyte activation, the in vitro LDL oxidation lag time was similar in renal patients and in healthy controls. It was concluded that the antioxidative defense of lipoproteins was preserved in renal failure and during dialysis.

In experimental models, antioxidants such as probucol and vitamin E were found to protect against glomeral injury (35, 36) and to slow atherogenic processes (28). Renal vasoconstriction caused by cholesterol feeding was corrected by probucol or by a thromboxane antagonist (35). Galle et al. (38) demonstrated that the inhibition of endothelium-dependent dilation induced by oxidized lipoprotein could be prevented by high density lipoproteins that are significantly decreased in hemodialyzed patients. In addition, minerals like selenium and nutrients such as coenzyme Q10 may minimize free radical generation and thus oxidative stress. Folic acid, vitamin B12 and vitamin B6 may be essential in the prevention of hyperhomocysteinemia that may contribute to the endothelial injury (39) and to oxidation of LDL (40) in these patients. A diet rich in mono-unsaturated fatty acids (oleic acid, resistant to oxidation) reduced the extent of endothelial injury in diabetes patients (41). Thus it is possible that dietary or pharmacological means may reduce OxLDL and aldehyde-modified LDL and von Willebrand factor in chronic renal failure and alleviate the enhanced generalized atherosclerosis in such patients.

After adjustment for the extent of renal failure, multiple regression analysis revealed that both LDL cholesterol levels and endothelial injury strongly contributed to the variations in OxLDL and aldehyde-modified LDL levels in severe chronic renal failure patients.

Hemodialysis results in platelet and leukocyte activation (42, 43), which generates oxygen radicals and aldehydes that may also contribute to oxidation of LDL. OxLDL and aldehyde-modified LDL may then contribute to thrombogenesis and atherogenesis by stimulating platelets (44). Because of the rather limited number of patients, subgroup analysis to further study the interaction between hemodialysis, oxidation of LDL and ischemic atherosclerotic disease could not be performed (45).

4. Legend to FIGS. 6 and 7

FIG. 6. Correlation between plasma levels of OxLDL and aldehyde-modified LDL (log values) and titers of autoantibodies (log values): regression line for severe chronic renal failure patients, either on conservative treatment (Δ; ---) (r=0.44; p=0.047) or on hemodialysis (□; ——) (r=0.37; p=0.0055). No significant correlation was observed in controls and in mild chronic renal failure patients.

FIG. 7. Correlation between plasma levels of OxLDL and aldehyde-modified LDL (log values) and of von Willebrand factor antigen (log values): regression line for mild chronic renal failure patients (○; -.-.-) (r=0.59; p=0.0057) or for severe chronic renal failure patients either on conservative treatment (Δ; ---) (r=0.69; p=0.0006) or on hemodialysis (□; ——) (r=0.62; p<0.00001). No significant correlation was observed in controls.

Example 8

Preparation of Reference-standard for Use in Immunological Assays

1. Introduction

According to the invention it has been found that LDL that is modified by treatment with malondialdehyde (MDA) is highly stable. Furthermore, the extent of modification is highly reproducible. LDL modified with MDA in a particular ratio has an identical number of substituted lysines and can therefore be used as a reference sample in immunological assays. This example shows the preparation of the standard.

2. Material and Methods

MDA-modified LDL was added to control plasma (containing anti-oxidants and anti-platelet compounds and anti-coagulants) to a final concentration of 100 nM MDA modified apo B-100. Aliquots were frozen at −80° C. In 6 days were aliquots were thawed, diluted to final concentrations ranging from 10 to 0.1 nM MDA-modified apo B-100 and analyzed in ELISA (4 dilution curves per. day).

3. Results

The inter-assay variation coefficients of 10 subsequent sandwich ELISA's of this invention using 10 subsequent, independent MDA-modified LDL standard preparations of this invention are summarized in Table 11.

These data show that for concentrations of MDA-modified LDL ranging from 10 and 0.01 nM the inter-assay variation ranged from 7.6 to 16.9%.

Abbreviations $C_{50}$: concentration required to obtain 50% inhibition of antibody binding
MDA: malondialdehyde
HEMO: severe chronic renal failure patients on maintenance hemodialysis
MCRF: mild chronic renal failure patients
SCRF: severe chronic renal failure patients on conservative treatment
OxLDL: oxidized low density lipoproteins.

TABLE 1

Clinical data of heart transplant patients

| Characteristics | Heart transplant patients | | |
|---|---|---|---|
| | Dilated cardio-myopathy (n = 47) | Ischemic heart disease (n = 60) | p-values |
| Age of recipient (yr) | 54 ± 1.6 | 55 ± 0.95 | *NS |
| Gender of recipient (M/F) | 41/6 | 53/7 | *NS |
| Age of donor (yr) | 29 ± 1.5 | 29 ± 1.4 | **NS |
| Gender of donor (M/F) | 31/16 | 44/16 | *NS |
| Length of follow up (mo) | 39 ± 3.1 | 50 ± 2.7 | **0.008 |
| Duration of ischemia (min) | 130 ± 7.0 | 140 ± 5.3 | **NS |
| No of HLA mismatches | | | |
| DR | 1.5 ± 0.09 | 1.4 ± 0.08 | **NS |
| B + DR | 3.1 ± 0.13 | 3.0 ± 0.13 | **NS |
| No of rejection episodes | 0.38 ± 0.13 | 0.25 ± 0.06 | **NS |
| Cytomegalovirus infection | 26 | 43 | *NS |
| Hypertension | 37 | 53 | *NS |
| Diabetes | 4 | 3 | *NS |

TABLE 1-continued

Clinical data of heart transplant patients

| | Heart transplant patients | | |
|---|---|---|---|
| Characteristics | Dilated cardio-myopathy (n = 47) | Ischemic heart disease (n = 60) | p-values |
| Coronary artery disease | | | |
| Grade 0 | 39 | 40 | *NS |
| Grade I | 5 | 13 | *NS |
| Grade II | 3 | 7 | *NS |
| Lipid lowering drugs | 17 | 39 | *0.004 |
| Statins | 13 | 33 | *0.006 |
| Fibrates | 4 | 6 | *NS |
| Calcium channel blockers | 31 | 47 | *NS |

Data represent mean ± SEM or number of patients.
*p-values determined by Chi-square test.
**p-values determined by Dunnett's multiple comparison test.
NS: not significant.

TABLE 2

Laboratory data of controls and heart transplant patients

| | | Heart transplant patients | | | | |
|---|---|---|---|---|---|---|
| | Controls | Dilated cardiomyopathy (DC) | | Ischemic heart disease | | |
| Characteristics | (n = 27) | (n = 47) | p vs control | (n = 60) | p s control | p-values vs DC |
| Serum triglyderides (mg/dl)† | 130 ± 11 | 130 ± 8.3 | NS | 140 ± 7.0 | NS | NS |
| HDL cholesterol (mg/dl)‡ | 44 ± 2.1 | 54 ± 2.5 | NS | 49 ± 1.9 | NS | NS |
| LDL cholesterol (mg/dl)‡ | 120 ± 4.7 | 100 ± 4.4 | NS | 110 ± 3.3 | NS | NS |
| Oxidized LDL (mg/dl) | 0.59 ± 0.036 | 1.3 ± 0.14 | <0.001 | 1.7 ± 0.13 | <0.001 | <0.01 |

Data represent mean ± SEM. p-values determined by Dunnett's multiple comparison test.
NS: not significant.
†to convert values for serum triglycerides to millimoles per liter, multiply by 0.011.
‡to convert values for serum cholesterol to millimoles per liter, muliply by 0.026.

TABLE 3

Logistic regression analysis of the relation between clinical-laboratory data and extent of coronary artery stenosis in heart transplant patients.

| Independent variable | Chi-square value | p-value |
|---|---|---|
| Oxidised LDL | 18 | 0.0001 |
| Length of follow up | 11 | 0.0008 |
| Age of donor | 3.9 | 0.047 |
| Age of recipient | 0.12 | 0.73 |
| Sex of recipient | 1.8 | 0.18 |
| Sex of donor | 0.025 | 0.88 |
| History of pretransplant dilated cardiomyopathy (n = 47) or ischemic heart disease (n = 60) | 0.0018 | 0.97 |
| Duration of ischemia | 0.25 | 0.62 |
| No of HLA mismatches | 1.6 | 0.20 |
| No of rejection episodes | 3.0 | 0.081 |
| Cytomegalovirus infection | 0.17 | 0.47 |
| Hypertension | 1.9 | 0.16 |
| Diabetes | 0.0016 | 0.97 |
| Treatment with lipid lowering drugs | | |
| Statins | 1.1 | 0.30 |
| Fibrates | 0.12 | 0.73 |
| Treatment with calcium channel blockers | 0.16 | 0.49 |

TABLE 3-continued

Logistic regression analysis of the relation between clinical-laboratory data and extent of coronary artery stenosis in heart transplant patients.

| Independent variable | Chi-square value | p-value |
|---|---|---|
| Serum triglycerides | 0.18 | 0.67 |
| Serum HDL cholesterol | 0.25 | 0.61 |
| Serum LDL cholesterol | 0.044 | 0.83 |

The data set contained 107 patients. Original cardiac disease was dilated cardiomyopathy in 47 and ischemic heart disease in 60 patients. Coronary artery stenosis was assessed angiographically. All quantitative parameters were transformed logarithmically to obtain a normal distribution for linear regression. Chi-square values were obtained after adjustment for all other variables.

TABLE 4

Clinical data of heart transplant patients without and with progression of coronary artery stenosis during a 3 years follow-up period.

| | Heart transplant patients | | |
|---|---|---|---|
| Characteristics | Without progression (n = 34) | With progression (n = 12) | p-value |
| Age of recipient (yr) | 58 ± 1.4 | 60 ± 1.4 | **NS |
| Gender of recipient (M/F) | 21/14 | 11/1 | *NS |
| Age of donor (yr) | 25 ± 1.3 | 32 ± 3.8 | **NS |
| Gender of donor (M/F) | 27/7 | 10/2 | *NS |
| Duration of ischemia (min) | 130 ± 6.7 | 140 ± 11 | **NS |
| No of HLA mismatches | | | |
| DR | 1.2 ± 0.13 | 1.5 ± 0.15 | **NS |
| B + DR | 2.8 ± 0.21 | 3.2 ± 0.24 | **NS |
| Cytomegalovirus infection | 24 | 11 | *NS |
| Hypertension | 21 | 10 | *NS |
| Diabetes | 1 | 2 | *NS |

Data represent mean ± SEM or number of patients.
*p-values determined by Chi-square analysis.
**p-values determined by Dunnett's multiple comparison test.
NS = not significant

TABLE 5

Laboratory data of heart transplant patients without and with progression of coronary artery stenosis during a 3 years follow-up period.

| Characteristics | Heart transplantation patients | | |
|---|---|---|---|
| | Without progression (n = 34) | With progression (n = 12) | p-value |
| Serum triglycerides (mg/dl) | 130 ± 8.6 | 150 ± 14 | NS |
| HDL cholesterol (mg/dl) | 50 ± 2.7 | 49 ± 4.9 | NS |
| LDL cholesterol (mg/dl) | 110 ± 3.6 | 105 ± 8.7 | NS |
| Oxidized LDL (mg/dl) | 1.2 ± 0.069 | 2.6 ± 0.33 | 0.0005 |

Data represent means ± SEM.
p-values determined by Dunnett's multiple regression comparison test.
NS = not significant.

TABLE 6

| Characteristics | Controls (n = 27) | Mild chronic renal failure (n = 20) | Severe chronic renal failure | |
|---|---|---|---|---|
| | | | non-dialysed (n = 21) | hemodialysed (n = 56) |
| Males/females | 12/15 | 11/9 | 7/14 | 33/23 |
| Age (years) | 54 (50–58)* | 52 (44–60)* | 55 (49–62)* | 61 (58–65)* |
| Body weight (kg) | 72 (69–76)* | 73 (67–79)* | 59 (53–65)* | 65 (61–68)* |
| Creatinine clearance (ml/min) | 110 (110–120)* | 34 (29–39)* | 8.4 (7–10)* | nd |
| Primary renal disease: | | | | |
| Glomerulonephritis | — | 4 | 3 | 11 |
| Autosomal dominant polycystic kidney disease | — | 2 | 6 | 10 |
| Diabetes | — | 1 | 4 | 6 |
| Reflux-nephropathy | — | 1 | 2 | 2 |
| Chronic Interstitial Nephritis | — | 2 | 2 | 9 |
| Hypertensive nephropathy | — | 2 | 0 | 2 |
| Other[1] | — | 6 | 1 | 9 |
| Unknown | — | 2 | 3 | 7 |
| Hypertension | 1 | 16 | 19 | 18 |
| Atherosclerotic heart disease | — | 6 | 7 | 24 |
| Cerebrovascular accidents | — | 0 | 3 | 9 |
| Peripheral vascular disease | — | 2 | 1 | 13 |

*Data represent means and 95% confidence intervals (between brackets).
[1]including: hereditary nephropathy, sarcoidosis, renal tuberculosis, thrombotic thrombocytopenic purpura, myeloma, traumatic loss, congenital urinary tract abnormalities.
nd: creatinine clearance rate cannot be determined adequately.

TABLE 7

Laboratory data of study subjects

| | Controls | MCRF patients | | SCRF patients | | HEMO patients | |
|---|---|---|---|---|---|---|---|
| | (n = 27) | (n = 20) | p vs controls | (n = 21) | p vs controls | (n = 56) | p vs controls |
| Triglycerides (mg/dl) | 120 (100–150) | 150 (130–170) | NS | 120 (100–140) | NS | 130 (110–160) | NS |
| HDL cholesterol (mg/dl) | 44 (39–48) | 38 (33–42) | NS | 44 (38–50) | NS | 37 (35–40) | <0.05 |
| LDL cholesterol (mg/dl) | 120 (110–130) | 110 (100–130) | NS | 110 (105–130) | NS | 120 (110–130) | NS |
| Oxidized LDL (mg/dl) | 0.59 (0.52–0.66) | 1.6 (1.0–2.2) | <0.01 | 1.8 (1.3–2.3) | <0.001 | 3.2 (2.7–3.7) | <0.001 |
| Autoantibodies (titer) | 4.2 (4.0–4.4) | 4.7 (4.0–5.4) | NS | 5.0 (4.2–5.8) | NS | 6.6 (5.7–7.4) | <0.001 |
| vWF (percent) | 100 (90–110) | 150 (110–180) | NS | 160 (130–190) | <0.01 | 210 (180–240) | <0.001 |

Data represent means and 95% confidence intervals (between brackets).

TABLE 8

Characteristics of native LDL and of OxLDL isolated from plasma of severe chronic renal failure patients

|  | Native LDL | OxLDL |
| --- | --- | --- |
| Protein/antigen ratio | >100 | 1.1 |
| Reactivity with mAb-4E6 ($C_{50}$ mg/dl) | 25 | 0.02 |
| Relative electrophoretic mobility | 1 | 1.7 |
| Malondialdehyde (mole/mole protein) | 3 | 68 |
| Substituted lysines per apo B-100 | 5 | 130 |
| Cholesterol/protein ratio | 1.8 | 3.3 |
| Free cholesterol/cholesterol ester ratio | 0.38 | 0.36 |
| Phospholipid/protein ratio | 1.7 | 1.6 |
| Fatty acids (%) | | |
| 16:0 | 14 | 37 |
| 18:1 | 19 | 50 |
| 18:2 | 55 | 10 |
| 20:4 | 12 | 3 |

Data represent means of ten LDL preparations of chronic renal failure patients. Native LDL and OxLDL patients were separated by ion-exchange chromatography.

TABLE 9

Multiple regression analysis of the dependence of OxLDL on the extent of renal failure

| Variable | F-value | p-value |
| --- | --- | --- |
| Age | 1.2 | 0.28 |
| Sex | 1.4 | 0.25 |
| Hypertension | 1.1 | 0.31 |
| Triglycerides | 1.5 | 0.23 |
| HDL cholesterol | 1.7 | 0.20 |
| LDL cholesterol | 0.99 | 0.32 |
| Renal failure | 14 | 0.0004 |

The data set contained 27 controls, 20 MCRF patients and 21 SCRF patients. F-values were obtained after adjustment for the other variables. Cockcroft creatinine clearance rates were used as a quantitative parameter for the extent of renal failure. All linear variables were logarithmically transformed to obtain normality for linear regression analysis. The multiple $R^2$ value of the multiple regression model was 0.634.

TABLE 10

Multiple regression analysis of the dependence of OxLDL on hemodialysis and LDL cholesterol levels in severe chronic renal failure patients

| Variable | F-value | p-value |
| --- | --- | --- |
| Age | 0.31 | 0.58 |
| Sex | 0.19 | 0.66 |
| Hypertension | 0.01 | 0.95 |
| HDL cholesterol | 0.02 | 0.89 |
| Triglycerides | 3.7 | 0.060 |
| Hemodialysis | 5.6 | 0.021 |
| LDL cholesterol | 7.1 | 0.0095 |

The data set contained 21 SCRF and 56 HEMO patients. All linear variables were transformed logarithmically to obtain normality for linear regression analysis. The multiple $R^2$ value of the multiple regression model was 0.56.

TABLE 11

Inter-assay variation coefficients of sandwich ELISA using 10 subsequent, independent MDA-modified LDL preparations

| Concentration (nM) | Inter-assay variations coefficients (%) |
| --- | --- |
| 10 | 9.6 |
| 5 | 7.6 |
| 2.5 | 8.4 |
| 1.25 | 13.2 |
| 0.62 | 12.0 |
| 0.31 | 13.0 |
| 0.16 | 12.3 |
| 0.08 | 15.5 |
| 0.04 | 16.9 |
| 0.02 | 13.6 |
| 0.01 | 11.4 |

Documents

1. Haberland M D, Fogelman A M, Edwards P A: Specificity of receptor-mediated recognition of malondialdehyde-modified low density lipoproteins. *Proc Natl Acad Sci* 1982;79:1712–1716.

2. Holvoet P, Collen D: Oxidized lipoproteins in atherosclerosis and thrombosis. *FASEB J* 1994;8:1279–8440.

3. Salonen J T, Ylä-Herttuala S, Yamamoto R, Butler S, Korpela H, Salonen R, Nyyssonen K, Palinski W, Witztum J L: Autoantibody against oxidized LDL and progression of carotid atherosclerosis. Lancet 339: 883–887, 1992.

4. Holvoet P, Perez G, Bernar H, Brouwers E, Vanloo B, Rosseneu M, Collen D: Stimulation with a monoclonal antibody (mAb4E4) of scavenger receptor-mediated uptake of chemically modified low density lipoproteins by THP-1 derived macrophages enhances foam cell generation. J Clin Invest 93: 89–98, 1994.

5. Holvoet P, Perez G, Zhao Z, Brouwers E, Bernar H, Collen D: Malondialdehyde-modified low density lipoproteins in patients with atherosclerotic disease. *J Clin Invest* 1995;95:2611–2619.

6. Havel R J, Eder H A, Bragdon J H: The distribution and chemical composition of ultracentrifugally separated lipoproteins in human sera. *J Clin Invest* 1955;34:1345–1353.

7. Steinbrecher U P: Oxidation of low density lipoprotein results in derivatization of lysine residues of apolipoprotein B by lipid peroxide decomposition products. *J Biol Chem* 1987;262:3603–3608.

8. Sparrow C P, Partharasathy S, Leake D S, Witztum J L, Steinberg D: Enzymatic modification of low density lipoprotein by purified lipoxygenase plus phospholipase-$A_2$ mimic cell-mediated oxidative modification. *J Lipid Res* 1988; 29: 745–753.

9. Holvoet P, Donck J, Landeloos M, Brouwers E, Luijtens K, Arnout J, Lesaffre E, Vanrenterghem Y, Collen D: Correlation between oxidized low density lipoproteins and von Willebrand factor in chronic renal failure. *Thromb Haemostas* 1996;76:663–669.

10. Libby P, Salomon R N, Payne D D, Schoen F J, Pober J S: Functions of vascular wall cells related to development of transplantation-associated coronary arteriosclerosis. *Transplant Proc* 1989;21:3677–3684.

11. Hruban R H, Beschorner W E, Baumgartner W A, Augustine S M, Ren H, Reitz B A, Hutchins G M: Accelerated arteriosclerosis in heart transplant recipients is associated with a T-lymphocyte-mediated endothelialitis. *Am J Pathol* 1990;137:871–882.

12. Rose E A, Smith C R, Petrossian G A, Barr M L, Reemtsma K: Humoral immune responses after cardiac transplantation: correlation with fatal rejection and graft atherosclerosis. *Surgery* 1989;106:203–208.

13. Tanaka H, Sukhova G K, Swanson S J, Cybulsky M I, Schoen F J, Libby P: Endothelial and smooth muscle cells express leukocyte adhesion molecules heterogeneously during acute rejection of rabbit cardiac allografts. *Am J Pathol* 1994;144:938–951.

14. Crisp S J, Dunn M J, Rose M L, Barbir M, Yacoub M H: Antiendothelial antibodies after heart transplantation: the accelerating factor in transplant-associated coronary artery disease? *J Heart Lung Transplant* 1994;13:81–92.

15. Grattan M T, Moreno-Cabral C E, Starnes V A, Oyer P E, Stinson E B, Shumway N E: Cytomegalovirus infection is associated with cardiac allograft rejection and atherosclerosis. *JAMA* 1989;261:3561–3566.

16. Koskinen P, Lemstrom K, Bruggeman C, Lautenschlager I, Hayry P: Acute cytomegalovirus infection induces a subendothelial inflammation (endothelialitis) in the allograft vascular wall. A possible linkage with enhanced allograft arteriosclerosis. *Am J Pathol* 1994;144:41–50.

17. Cartier R, Dagenais F, Hollmann C, Cambron H, Buluran J: Chronic exposure to cyclosporin affects endothelial and smooth muscle reactivity in the rat aorta. *Ann Thorac Surg* 1994;58:789–794.

18. Chin J H, Azhar S, Hoffman B B: Inactivation of endothelial derived relaxing factor by oxidized lipoproteins. *J. Clin. Invest.* 1992;89:10–18.

19. Galle J, Schollmeyer P, Wanner C: Cyclosporin and oxidized low density lipoproteins synergistically potentiate vasoconstriction: influence of the endothelium. *Eur Heart J* 1993;14(Suppl):111–117.

20. Tuzcu E M, Hobbs R E, Rincon G, Bott-Silverman C, De Franco A C, Robinson K, McCarthy P M, Stewart R W, Guyer S, Nissen S E: Occult and frequent transmission of atherosclerotic coronary disease with cardiac transplantation. Insights from intravascular ultrasound. *Circulation* 1995;91:1706–1713.

21. Hoff H F, O'Neill: Lesion-derived low density lipoprotein and oxidized low density lipoprotein share a lability for aggregation, leading to enhanced macrophage degradation. *Arterioscler Thromb* 1991; 11:1209–1222.

22. Steinbrecher U P, Lougheed M: Scavenger receptor-independent stimulation of cholesterol esterification in macrophages by low density lipoprotein extracted from human aortic intima. *Arterioscler Thromb* 1992; 12:608–625 33. Steinberg D, Witztum J L: Lipoproteins and atherogenesis: current concepts. *J Am Med Assoc* 1990;264:3047–3052.

23. Ross R: The pathogenesis of atherosclerosis: a perspective for the 1990s. *Nature* 1993;362:801–809.

24. Murugesan G, Chisolm G M, Fox P L: Oxidized low density lipoprotein inhibits the migration of aortic endothelial cells in vitro. *J Cell Biol* 1993; 120: 1011–1019.

25. Chen C H, Nguyen H H, Weilbaecher D, Luo S, Gotto A M Jr, Henry P D: Basic growth factor reverses atherosclerotic impairment of human coronary angiogenesis-like responses in vitro. *Atherosclerosis* 1995; 116: 261–268.

26. Juckett M B, Balla J, Balla G, Jessurun J, Jacob H S, Vercellotti G M: Ferritin protects endothelial cells from oxidized low density lipoprotein in vitro. *Am J Pathol* 1995;147:782–789.

27. Mabile L, Fitoussi G, Periquet B, Schmitt A, Salvayre R, Negre-Salvayre A: Alpha-Tocopherol and trolox block the early intracellular events (TBARS and calcium rises) elicited by oxidized low density lipoproteins in cultured endothelial cells. *Free Radic Biol Med* 1995;19:177–187.

28. Steinberg D: Clinical trials of antioxidants in atherosclerosis: are we doing the right thing? *Lancet* 1995;346: 36–38.

29. Degoulet P, Legrain M, Reach I, Aime F, Devries C, Rojas P, Jacobs C: Mortality risk factors in patients treated by chronic hemodialysis. Nephron 31: 103–110, 1982.

30. Neff M S, Eiser A R, Slifkin R F, Baum M, Baez A, Gupta S, Amarga E: Patients surviving 10 years of hemodialysis. Am J Med 74: 996–1004, 1983.

31. Cockcroft D W, Gault M H: Prediction of creatinine clearance from serum creatinine. Nephron 16: 31–41, 1976.

32. Reade V, Tailleux A, Reade R, Harduin P, Cachera C, Tacquet A, Fruchart J C, Fievet C: Expression of apolipoprotein B epitopes in low density lipoproteins of hemodialyzed patients. Kidney Int 44: 1360–1365, 1993.

33. Sutherland W H, Walker R J, Ball M J, Stapley S A, Robertson M C: Oxidation of low density lipoproteins from patients with renal failure or renal transplants. Kidney Int 48: 227–236, 1995.

34. Schulz T, Schiffl H, Scheithe R, Hrboticky N, Lorenz R: Preserved antioxidative defense of lipoproteins in renal failure and during hemodialysis. Am J Kidney Dis 25: 564–571, 1995.

35. Keane W F, Mulcahy W S, Kasiske B L, Kim Y, O'Donnell M P: Hyperlipidemia and progressive renal disease. Kidney Int Suppl 39: S41–S48, 1991.

36. Trachtman H. Schwob N, Maesaka J, Valderrama E: Dietary supplementation ameliorates renal injury in chronic puromycin aminonucleoside nephropathy. J Am Soc Nephrol 5: 1811–1819, 1995.

37. Kaplan R, Aynedjian H S, Schlondorff D, Bank N: Renal vasoconstriction caused by short-term cholesterol feeding is corrected by thromboxane antagonist or probucol. J Clin Invest 86: 1707–1714, 1990.

38. Galle J, Bengen J, Schollmeyer P, Wanner C: Oxidized lipoprotein(a) inhibits endothelium-dependent dilation: prevention by high density lipoprotein. Eur J Pharmacol 265: 111–115, 1994.

39. Friedman J A, Dwyer J T: Hyperhomocysteinemia as a risk factor for cardiovascular disease in patients undergoing hemodialysis. Nutr Rev 53: 197–201, 1995.

40. McCully K S: Chemical pathology of homocysteine. I. Atherogenesis. Ann Clin Lab Sci 23: 477–493, 1993.

41. Rasmussen O, Thomsen C, Ingerslev J, Hermansen K: Decrease of von Willebrand factor levels after a high-monounsaturated fat diet in non-insulin-dependent diabetic subjects. Metabolism 43: 1406–1409, 1994.

42. Reverter J C, Escolar G. Sanz C, Cases A, Villamor N, Nieuwenhuis HK, Lopez J, Ordinas A: Platelet activation during hemodialysis measured through exposure of P-selec- 43. Zwaginga J J, Koomans H A, Sixma J J, Rabelink T J: Thrombus formation and platelet-vessel wall interaction in the nephrotic syndrome under flow conditions. J Clin Invest 93: 204–211, 1994.

44. Zhao B, Dierichs R, Harrachruprecht B, Winterhorff H: Oxidized LDL induces serotonin release from blood platelets. Am J Hematol 48: 285–287, 1995.

45. Pocock S J: Subgroup analysis, in Pocock S J (ed): Clinical trial. A practical approach. Wiley J & Sons, Chichester, 1993, p 211–218.

The invention claimed is:

1. Monoclonal antibody mAb-4E6 produced by hybridoma Hyb4E6 deposited at the BCCM under deposit accession number LMBP 1660 CB on Apr. 24, 1997.

2. Hybridoma Hyb4E6 deposited at the BCCM under deposit accession number LMBP 1660 CB on Apr. 24, 1997.

* * * * *